(12) United States Patent
Nguyen et al.

(10) Patent No.: US 12,134,779 B2
(45) Date of Patent: Nov. 5, 2024

(54) HYDROGEL PARTICLES AS FEEDER CELLS AND AS SYNTHETIC ANTIGEN PRESENTING CELLS

(71) Applicant: Slingshot Biosciences, Inc., Emeryville, CA (US)

(72) Inventors: Anh Tuan Nguyen, San Francisco, CA (US); Jeffrey Kim, Berkeley, CA (US); Keunho Ahn, Pleasanton, CA (US); Daixuan Zhang, Fremont, CA (US)

(73) Assignee: Slingshot Biosciences, Inc., Emeryville, CA (US)

( * ) Notice: Subject to any disclaimer, the term of this patent is extended or adjusted under 35 U.S.C. 154(b) by 0 days.

(21) Appl. No.: 18/386,107

(22) Filed: Nov. 1, 2023

(65) Prior Publication Data

US 2024/0060038 A1  Feb. 22, 2024

Related U.S. Application Data

(63) Continuation of application No. PCT/US2022/048283, filed on Oct. 28, 2022.

(60) Provisional application No. 63/320,016, filed on Mar. 15, 2022, provisional application No. 63/320,009, filed on Mar. 15, 2022, provisional application No. 63/274,316, filed on Nov. 1, 2021, provisional application No. 63/273,741, filed on Oct. 29, 2021.

(51) Int. Cl.
*C12N 5/00* (2006.01)
*C12M 1/42* (2006.01)

(52) U.S. Cl.
CPC ........... *C12N 5/0018* (2013.01); *C12M 35/06* (2013.01); *C12N 2500/50* (2013.01)

(58) Field of Classification Search
None
See application file for complete search history.

(56) References Cited

U.S. PATENT DOCUMENTS

| | | | |
|---|---|---|---|
| 3,822,095 | A | 7/1974 | Hirschfeld |
| 3,872,312 | A | 3/1975 | Hirschfeld |
| 3,916,205 | A | 10/1975 | Kleinerman |
| 3,937,799 | A | 2/1976 | Lewin et al. |
| 3,947,564 | A | 3/1976 | Shannon et al. |
| 3,975,084 | A | 8/1976 | Block |
| 4,271,123 | A | 6/1981 | Curry et al. |
| 4,295,199 | A | 10/1981 | Curry et al. |

(Continued)

FOREIGN PATENT DOCUMENTS

| | | |
|---|---|---|
| CN | 101214217 A | 7/2008 |
| CN | 101245368 A | 8/2008 |

(Continued)

OTHER PUBLICATIONS

Liu, Z. et al. Recent Advances on Magnetic Sensitive Hydrogels in Tissue Engineering, Frontiers in Chemistry, Mar. 2020, vol. 8, Article 124 (Year: 2020).*

(Continued)

*Primary Examiner* — Xiaoyun R Xu
(74) *Attorney, Agent, or Firm* — COOLEY LLP

(57) ABSTRACT

The present disclosure provides feeder hydrogel particles that can function to support the growth, proliferation, and/or activation of a target cell in culture. The present disclosure also provides methods of culturing target cells with feeder hydrogel particles.

17 Claims, 14 Drawing Sheets

(56) References Cited

U.S. PATENT DOCUMENTS

| | | | |
|---|---|---|---|
| 4,389,491 A | 6/1983 | Hanamoto et al. |
| 4,409,335 A | 10/1983 | Hanamoto et al. |
| 4,448,888 A | 5/1984 | Bleile et al. |
| 4,511,662 A | 4/1985 | Baran et al. |
| 4,704,891 A | 11/1987 | Recktenwald et al. |
| 4,774,189 A | 9/1988 | Schwartz |
| 4,857,451 A | 8/1989 | Schwartz |
| 5,093,234 A | 3/1992 | Schwartz |
| 5,244,799 A | 9/1993 | Anderson |
| 5,283,079 A | 2/1994 | Wang et al. |
| 5,395,688 A | 3/1995 | Wang et al. |
| 5,820,879 A | 10/1998 | Fernandez et al. |
| 5,841,139 A | 11/1998 | Sostek et al. |
| 5,871,722 A | 2/1999 | Nacht et al. |
| 5,888,823 A | 3/1999 | Matsumoto et al. |
| 6,043,506 A | 3/2000 | Heffelfinger et al. |
| 6,107,365 A | 8/2000 | Bertozzi et al. |
| 6,108,082 A | 8/2000 | Pettipiece et al. |
| 6,214,539 B1 | 4/2001 | Cosand |
| 6,280,618 B2 | 8/2001 | Watkins et al. |
| 6,372,813 B1 | 4/2002 | Johnson et al. |
| 6,516,537 B1 | 2/2003 | Teich et al. |
| 6,586,176 B1 | 7/2003 | Trnovsky et al. |
| 6,657,030 B2 | 12/2003 | Vanderbilt |
| 6,762,055 B2 | 7/2004 | Carver et al. |
| 6,806,058 B2 | 10/2004 | Jesperson et al. |
| 6,872,578 B2 | 3/2005 | Watkins et al. |
| 6,897,072 B1 | 5/2005 | Rich et al. |
| 7,045,366 B2 | 5/2006 | Huang et al. |
| RE39,542 E | 4/2007 | Jain et al. |
| 7,205,156 B2 | 4/2007 | Rich et al. |
| 7,294,503 B2 | 11/2007 | Quake et al. |
| 7,314,584 B2 | 1/2008 | Tsutsui et al. |
| 7,465,538 B2 | 12/2008 | Watkins et al. |
| 7,479,631 B2 | 1/2009 | Rich et al. |
| 7,482,161 B2 | 1/2009 | Carver et al. |
| 7,482,167 B2 | 1/2009 | Sammak et al. |
| 7,531,357 B2 | 5/2009 | Carver et al. |
| 7,569,399 B2 | 8/2009 | Watkins et al. |
| 7,588,942 B2 | 9/2009 | Ho et al. |
| 7,601,539 B2 | 10/2009 | Kawate |
| 7,776,927 B2 | 8/2010 | Chu et al. |
| 7,842,498 B2 | 11/2010 | Um et al. |
| 8,030,095 B2 | 10/2011 | Harriman |
| 8,105,845 B2 | 1/2012 | Notcovich et al. |
| 8,114,580 B2 | 2/2012 | Carver et al. |
| 8,187,885 B2 | 5/2012 | Purvis, Jr. |
| 8,415,161 B2 | 4/2013 | Yan et al. |
| 8,415,173 B2 | 4/2013 | Harriman |
| 8,451,450 B2 | 5/2013 | Heng |
| 8,580,530 B2 | 11/2013 | Buffiere et al. |
| 8,580,531 B2 | 11/2013 | Buffiere et al. |
| 8,603,828 B2 | 12/2013 | Walker et al. |
| 8,609,363 B2 | 12/2013 | Heng et al. |
| 8,704,158 B2 | 4/2014 | Haberstroh et al. |
| 8,748,183 B2 | 6/2014 | Durack et al. |
| 9,012,167 B2 | 4/2015 | Dallenne et al. |
| 9,110,050 B2 | 8/2015 | Likuski et al. |
| 9,175,421 B2 | 11/2015 | Notcovich et al. |
| 9,176,154 B2 | 11/2015 | Darmstadt et al. |
| 9,213,034 B2 | 12/2015 | Walker et al. |
| 9,217,175 B2 | 12/2015 | Regan et al. |
| 9,228,898 B2 | 1/2016 | Kiani et al. |
| 9,417,190 B2 | 8/2016 | Hindson et al. |
| 9,476,101 B2 | 10/2016 | Pregibon et al. |
| 9,658,220 B2 | 5/2017 | King et al. |
| 9,696,257 B2 | 7/2017 | Fox et al. |
| 9,714,897 B2 | 7/2017 | Kim et al. |
| 9,804,149 B2 | 10/2017 | Darmstadt et al. |
| 9,816,931 B2 | 11/2017 | Abate et al. |
| 9,915,598 B2 | 3/2018 | Kim et al. |
| 10,067,135 B2 | 9/2018 | Kaul et al. |
| 10,180,385 B2 | 1/2019 | Fox et al. |
| 10,191,039 B2 | 1/2019 | King et al. |
| 10,343,167 B2 | 7/2019 | Esmail et al. |
| 10,344,100 B1 * | 7/2019 | Vashist | G01N 33/54346 |
| 10,392,557 B2 | 8/2019 | Chan |
| 10,416,070 B1 | 9/2019 | Handique |
| 10,429,291 B2 | 10/2019 | Fox et al. |
| 10,481,068 B2 | 11/2019 | Kim et al. |
| 10,508,990 B2 | 12/2019 | Fox et al. |
| 10,732,189 B2 | 8/2020 | Buffiere et al. |
| 10,753,846 B2 | 8/2020 | Kim et al. |
| 10,942,109 B2 | 3/2021 | Kim et al. |
| 11,047,845 B1 | 6/2021 | Barry, Jr. et al. |
| 11,085,036 B2 | 8/2021 | Norberg et al. |
| 11,118,217 B2 | 9/2021 | Xue et al. |
| 11,155,809 B2 | 10/2021 | Lebofsky |
| 11,180,752 B2 | 11/2021 | Wu et al. |
| 11,186,862 B2 | 11/2021 | Lebofsky et al. |
| 11,213,490 B2 | 1/2022 | Shoichet et al. |
| 11,231,355 B2 | 1/2022 | Handique |
| 11,274,337 B2 | 3/2022 | Xue et al. |
| 11,300,496 B2 | 4/2022 | Handique |
| 11,313,782 B2 | 4/2022 | Kim et al. |
| 11,479,816 B2 | 10/2022 | Lebofsky et al. |
| 11,506,655 B2 | 11/2022 | Hunsley et al. |
| 11,598,768 B2 | 3/2023 | Kim |
| 11,603,556 B2 | 3/2023 | Lebofsky |
| 11,663,717 B2 | 5/2023 | Barnes et al. |
| 11,686,661 B2 | 6/2023 | Kim et al. |
| 11,726,023 B2 | 8/2023 | Kim et al. |
| 11,747,261 B2 | 9/2023 | Kim et al. |
| 11,761,877 B2 | 9/2023 | Kim et al. |
| 11,927,519 B2 | 3/2024 | Kim et al. |
| 2001/0008217 A1 | 7/2001 | Watkins et al. |
| 2001/0054580 A1 | 12/2001 | Watkins et al. |
| 2002/0106730 A1 | 8/2002 | Coyle et al. |
| 2002/0115116 A1 | 8/2002 | Song et al. |
| 2003/0013116 A1 | 1/2003 | Song et al. |
| 2003/0022157 A1 | 1/2003 | Zauderer et al. |
| 2003/0064403 A1 | 4/2003 | Song et al. |
| 2003/0124371 A1 | 7/2003 | Um et al. |
| 2003/0132538 A1 | 7/2003 | Chandler |
| 2003/0190749 A1 | 10/2003 | Surber et al. |
| 2003/0218130 A1 | 11/2003 | Boschetti et al. |
| 2003/0224444 A1 | 12/2003 | Sabbadini et al. |
| 2003/0232323 A1 | 12/2003 | Freeman et al. |
| 2004/0126904 A1 | 7/2004 | Watkins et al. |
| 2004/0137577 A1 | 7/2004 | Coyle et al. |
| 2005/0059086 A1 | 3/2005 | Huang et al. |
| 2005/0090016 A1 | 4/2005 | Rich et al. |
| 2005/0112650 A1 | 5/2005 | Chang et al. |
| 2005/0118230 A1 | 6/2005 | Hill et al. |
| 2005/0172476 A1 | 8/2005 | Stone et al. |
| 2005/0176056 A1 | 8/2005 | Sammak et al. |
| 2005/0208573 A1 | 9/2005 | Bell et al. |
| 2006/0163385 A1 | 7/2006 | Link et al. |
| 2006/0223187 A1 | 10/2006 | Carver et al. |
| 2006/0240560 A1 | 10/2006 | Bakker et al. |
| 2006/0250616 A1 | 11/2006 | Pettipiece et al. |
| 2006/0269962 A1 | 11/2006 | Watkins et al. |
| 2006/0275820 A1 | 12/2006 | Watkins et al. |
| 2007/0000342 A1 | 1/2007 | Kazuno |
| 2007/0003442 A1 | 1/2007 | Link et al. |
| 2007/0054119 A1 | 3/2007 | Garstecki et al. |
| 2007/0082019 A1 | 4/2007 | Huang et al. |
| 2007/0087348 A1 | 4/2007 | Notcovich et al. |
| 2007/0158547 A1 | 7/2007 | Rich et al. |
| 2007/0178168 A1 | 8/2007 | Ho et al. |
| 2007/0254378 A1 | 11/2007 | Zhang et al. |
| 2007/0259415 A1 | 11/2007 | Zigova et al. |
| 2008/0014589 A1 | 1/2008 | Link et al. |
| 2008/0019921 A1 | 1/2008 | Zhang |
| 2008/0023630 A1 | 1/2008 | Boschetti et al. |
| 2008/0026468 A1 | 1/2008 | Carver et al. |
| 2008/0032405 A1 | 2/2008 | Ho et al. |
| 2008/0044472 A1 | 2/2008 | Garcia et al. |
| 2008/0090737 A1 | 4/2008 | Boschetti |
| 2008/0241262 A1 | 10/2008 | Lee et al. |
| 2009/0148961 A1 | 6/2009 | Luchini et al. |
| 2010/0120059 A1 | 5/2010 | Yan et al. |
| 2010/0178647 A1 | 7/2010 | Carver et al. |
| 2010/0178656 A1 | 7/2010 | Buffiere et al. |

(56) References Cited

U.S. PATENT DOCUMENTS

| | | |
|---|---|---|
| 2010/0184101 A1 | 7/2010 | Buffiere et al. |
| 2010/0187441 A1 | 7/2010 | Waldbeser et al. |
| 2010/0234252 A1 | 9/2010 | Moradi-Araghi et al. |
| 2010/0285594 A1 | 11/2010 | Purvis, Jr. |
| 2010/0303811 A1 | 12/2010 | Ochi |
| 2011/0117670 A1 | 5/2011 | Walker et al. |
| 2011/0218123 A1 | 9/2011 | Weitz et al. |
| 2011/0222068 A1 | 9/2011 | Heng |
| 2011/0318820 A1 | 12/2011 | Hinz et al. |
| 2012/0129723 A1 | 5/2012 | Notcovich et al. |
| 2012/0295300 A1 | 11/2012 | Heng et al. |
| 2012/0309651 A1 | 12/2012 | Pregibon et al. |
| 2013/0089883 A1 | 4/2013 | Dallenne et al. |
| 2013/0177973 A1 | 7/2013 | Kondo |
| 2013/0274125 A1 | 10/2013 | Binder et al. |
| 2014/0073532 A1 | 3/2014 | Walker et al. |
| 2014/0100791 A1 | 4/2014 | Darmstadt et al. |
| 2014/0157859 A1 | 6/2014 | Darmstadt et al. |
| 2014/0179808 A1 | 6/2014 | Flanagan |
| 2014/0198313 A1 | 7/2014 | Tracy et al. |
| 2014/0221238 A1 | 8/2014 | Regan et al. |
| 2014/0271677 A1 | 9/2014 | Palese et al. |
| 2014/0377334 A1* | 12/2014 | Irvine ............. A61K 9/1271 424/490 |
| 2015/0027207 A1 | 1/2015 | Likuski et al. |
| 2015/0094232 A1 | 4/2015 | Abate et al. |
| 2015/0177115 A1 | 6/2015 | Kim et al. |
| 2015/0211044 A1 | 7/2015 | Dallenne et al. |
| 2015/0267196 A1 | 9/2015 | Alsberg et al. |
| 2016/0258856 A1 | 9/2016 | Kim et al. |
| 2017/0045436 A1 | 2/2017 | Fox et al. |
| 2017/0159132 A1 | 6/2017 | Okino et al. |
| 2017/0268998 A1 | 9/2017 | Fox et al. |
| 2017/0361322 A1 | 12/2017 | Esmail et al. |
| 2017/0370951 A1 | 12/2017 | Buffiere et al. |
| 2018/0172687 A1 | 6/2018 | Kaul et al. |
| 2018/0216171 A1 | 8/2018 | Xue et al. |
| 2018/0275040 A1 | 9/2018 | Kim et al. |
| 2018/0371525 A1 | 12/2018 | Lebofsky et al. |
| 2019/0145881 A1 | 5/2019 | Fox et al. |
| 2019/0154707 A1 | 5/2019 | Flamini et al. |
| 2019/0249171 A1 | 8/2019 | Wu et al. |
| 2019/0293546 A1 | 9/2019 | Handique |
| 2020/0056231 A1 | 2/2020 | Lebofsky et al. |
| 2020/0085971 A1 | 3/2020 | Kevlahan et al. |
| 2020/0115675 A1 | 4/2020 | Pathak et al. |
| 2020/0150020 A1 | 5/2020 | Kim et al. |
| 2020/0206145 A1 | 7/2020 | Shi et al. |
| 2020/0209064 A1 | 7/2020 | Owsley et al. |
| 2020/0232979 A1 | 7/2020 | Revzin et al. |
| 2020/0249242 A1 | 8/2020 | Batxelli-Molina et al. |
| 2020/0268845 A1 | 8/2020 | Peled et al. |
| 2020/0332354 A1 | 10/2020 | Xue et al. |
| 2020/0363434 A1 | 11/2020 | Buffiere et al. |
| 2020/0399428 A1 | 12/2020 | Kleine-Brüggeney et al. |
| 2020/0400546 A1 | 12/2020 | Kim et al. |
| 2020/0408747 A1 | 12/2020 | Zur Megede et al. |
| 2021/0040567 A1 | 2/2021 | Handique et al. |
| 2021/0130880 A1 | 5/2021 | Lebofsky |
| 2021/0190740 A1 | 6/2021 | Scolari et al. |
| 2021/0231552 A1 | 7/2021 | Kim et al. |
| 2021/0247294 A1 | 8/2021 | Handique |
| 2021/0341469 A1 | 11/2021 | Kim et al. |
| 2022/0042077 A1 | 2/2022 | Lebofsky et al. |
| 2022/0065878 A1 | 3/2022 | Lee |
| 2022/0154266 A1 | 5/2022 | Xue et al. |
| 2022/0178810 A1 | 6/2022 | Kim et al. |
| 2022/0213530 A1 | 7/2022 | Larson et al. |
| 2022/0260476 A1 | 8/2022 | Kim et al. |
| 2022/0364976 A1 | 11/2022 | Kim et al. |
| 2023/0012786 A1 | 1/2023 | Lebofsky et al. |
| 2023/0062518 A1 | 3/2023 | Ebrahim et al. |
| 2023/0067460 A1 | 3/2023 | Nguyen et al. |
| 2023/0152202 A1 | 5/2023 | Kim et al. |
| 2023/0176042 A1 | 6/2023 | Kim et al. |
| 2023/0266223 A1 | 8/2023 | Kim et al. |
| 2024/0053248 A1 | 2/2024 | Kim et al. |

FOREIGN PATENT DOCUMENTS

| | | | |
|---|---|---|---|
| CN | 103744185 A | 4/2014 | |
| CN | 104641217 A | 5/2015 | |
| EP | 3585364 A1 | 1/2020 | |
| JP | H07196916 A | 8/1995 | |
| JP | 2002510541 A | 4/2002 | |
| JP | 2005281470 A | 10/2005 | |
| JP | 2007114026 A | 5/2007 | |
| JP | 2010265291 A | 11/2010 | |
| JP | 2012011269 A | 1/2012 | |
| JP | 2013520530 A | 6/2013 | |
| JP | 2013155358 A | 8/2013 | |
| JP | 2014058557 A | 4/2014 | |
| JP | 2014508516 A | 4/2014 | |
| JP | 2015530361 A | 10/2015 | |
| WO | WO-8910566 A1 | 11/1989 | |
| WO | WO-1995003408 A1 | 2/1995 | |
| WO | WO-0008212 A1 | 2/2000 | |
| WO | WO-0132829 A2 | 5/2001 | |
| WO | WO-03000014 A2 | 1/2003 | |
| WO | WO-2005013896 A2 | 2/2005 | |
| WO | WO-2006003423 A2 | 1/2006 | |
| WO | WO-2006078841 A1 | 7/2006 | |
| WO | WO-2006096571 A2 | 9/2006 | |
| WO | WO-2007101130 A2 | 9/2007 | |
| WO | WO-2008115653 A2 | 9/2008 | |
| WO | WO-2008121342 A2 | 10/2008 | |
| WO | WO-2010025190 A1 | 3/2010 | |
| WO | WO-2010025988 A1 | 3/2010 | |
| WO | WO-2011098407 A1 | 8/2011 | |
| WO | WO-2012033811 A1 | 3/2012 | |
| WO | WO-2013113670 A1 | 8/2013 | |
| WO | WO-2014089009 A1 | 6/2014 | |
| WO | WO 2016/130489 * | 8/2016 | ............. G01N 33/22 |
| WO | WO-2018108341 A1 | 6/2018 | |
| WO | WO-2020037214 A1 | 2/2020 | |
| WO | WO-2021154900 A1 | 8/2021 | |
| WO | WO-2023215886 A1 | 11/2023 | |
| WO | WO-2024092161 A2 | 5/2024 | |

OTHER PUBLICATIONS

Jain, P. et al. Zwitterionic Hydrogels Based on a Degradable Disulfide Carboxybetaine Cross-Linker, Langmuir 2019, 35, 1864-1871 (Year: 2019).*

Atkin-Smith et al., "Isolation of cell type-specific apoptotic bodies by fluorescence-activated cell sorting," Scientific Reports, vol. 7, No. 1, Feb. 1, 2017, pp. 1-7.

Bele, Marjan, Olavi Siiman and Egon Matjevic, "Preparation and flow cytometry of uniform silica-fluorescent dye microspheres." Journal of colloid and interface science 254(2):274-282 (2002).

Chen, M., et al., "Initiator caspases in apoptosis signaling pathways", Apoptosis (London), Aug. 1, 2002, pp. 313-319, DOI: 10.1023/A:1016167228059.

Co-pending U.S. Appl. No. 18/213,934, inventors Kim; Jeffrey et al., filed Jun. 26, 2023.

Extended European Search Report issued by the European Patent Office for Application No. 16749674.4, dated Sep. 6, 2018, 12 pages.

Gaulding, et al., "Reversible Inter- and Intra-microgel Cross-linking Using Disulfides," Macromolecules, 2012, vol. 45(1), pp. 39-45.

Hasegawa, Urara et al. "Nanogel-quantum dot hybrid nanoparticles for live cell imaging." Biochemical and biophysical research communications 331(4):917-921 (2005).

Higuchi, A., et al., "Design of polymeric materials for culturing human pluripotent stem cells: Progress toward feeder-free and xeno-free culturing," Progress in Polymer Science, Jul. 2014, vol. 39 (7), pp. 1348-1374.

International Search Report and Written Opinion for International Application No. PCT/US2022/048283 dated Feb. 14, 2023, 14 pages.

(56) References Cited

OTHER PUBLICATIONS

International Search Report and Written Opinion for International Patent Application No. PCT/US2016/017029, mailed May 19, 2016, 8 pages.
International Search Report and Written Opinion for International Patent Application No. PCT/US21/014538, dated Apr. 8, 2021, 19 pages.
International Search Report and Written Opinion for International Patent Application No. PCT/US21/030590, dated Jul. 26, 2021, 13 pages.
International Search Report and Written Opinion for PCT Application No. PCT/US2023/066684 dated Aug. 7, 2023, 15 pages.
International Search Report and Written Opinion for PCT Application No. PCT/US2023/067893 dated Oct. 10, 2023, 22 pages.
Jin, Z., et al., "Overview of cell death 1-124 signaling pathways", Cancer Biology &G Therapy, vol. 4, No. 2, Feb. 2, 2005, pp. 147-171, DOI: 10.4161/cbt.4.2.1508.
Kim, Jin-Woong et al., "Fabrication of Monodisperse Gel Shells and Functional Microgels in Microfluidic Devices," Angew. Chem. Int. Ed. 46:819-1822 (2007).
Lee, Ki-Chang and Lee, Sang-Yun, "Preparation of Highly Cross-Linked, Monodisperse Poly (methyl methacrylate) Microspheres by Dispersion Polymerization; Part II. Semi-continuation Processes," Macromolecular Research 6(4):293-302 (2008).
Liu, A.L., et al., "Methods for Generating Hydrogel Particles for Protein Delivery," Annals of Biomedical Engineering, Jun. 2016, vol. 44 (6), pp. 1946-1958.
Luchini, Alessandra et al. "Smart hydrogel particles: biomarker harvesting: one-step affinity purification, size exclusion, and protection against degradation." Nano letters 8(1): 350-361 (2008).
Patanarut, Alexis et al., "Synthesis and characterization of hydrogel particles containing Cibacron Blue F3G-A." Colloids and Surfaces A: Physicochemical and Engineering Aspects 362(1):8-19 (2010).
Perez-Luna, V.H., et al., "Encapsulation of Biological Agents in Hydrogels for Therapeutic Applications," Gels, Jul. 11, 2018, vol. 4 (3), pp. 61.
Proll, Guenther et al. "Potential of label-free detection in high-content-screening applications." Journal of Chromatography A 1116(1):2-8 (2007).
Shastri, V.P., et al., "Non-Degradable Biocompatible Polymers in Medicine: Past, Present and Future", Current Pharmaceutical Biotechnology, Bentham Science Publishers, NL, vol. 4, No. 5, Jan. 1, 2003, pp. 331-337.
Tomczak, Nikodem et al., "Designer polymer-quantum dot architectures." Progress in Polymer Science 34:393-430 (2009).
Ugelstad, J. and Mork, P.C., "Swelling of Oligomer-Polymer Particles. New Methods of Preparation of Emulsions and Polymer Dispersions," Advances in Colloid and Interface Sciences, 13:101-140 (1980).
Wallberg et al., "Analysis of Apoptosis and Necroptosis by Fluorescence-Activated Cell Sorting," Cold Spring Harbor Protocol, vol. 2016, No. 4, Apr. 1, 2016, 7 pages.
Extended European Search Report for European Application No. EP21744765.5 dated Jan. 29, 2024, 8 pages.
Co-pending U.S. Appl. No. 18/417,986, inventors Jeffrey; Kim et al., filed Jan. 19, 2024.
International Search Report and Written Opinion for International Application No. PCT/US2023/075041 dated Mar. 8, 2024, 11 pages.
Chen et al., "Molecular mechanisms of T cell co-stimulation and co-inhibition," Nature reviews Immunology, 13:227-242 (2013).
Claus et al., "The emerging landscape of novel 4-1BB (CD137) agonistic drugs for cancer immunotherapy," MAbs 15(1):2167189, pp. 1-22 (Jan.-Dec. 2023).
Elbert, "Liquid-liquid two-phase systems for the production of porous hydrogels and hydrogel microspheres for biomedical applications: A tutorial review," Acta Biomater. 7(1):31-56 (Jan. 2011). Epub Jul. 24, 2010.
Hegelson et al., "Hydrogel microparticles from lithographic processes: novel materials for fundamental and applied colloid science," Curr. Opin. Colloid. Interface Sci. 16(2):106-117 (Apr. 1, 2011).
Heller et al., "inylcarbonates and vinylcarbamates: Biocompatible monomers for radical photopolymerization," Journal of Polymer Science Part A: Polymer Chemistry 49, pp. 650-661 (Dec. 2, 2010).
Hu and Messersmith, "Rational design of transglutaminase substrate peptides for rapid enzymatic formation of hydrogels,". J Am. Chem. Soc. 125, 14298-14299 (Oct. 31, 2003).
Lutolf et al., "Synthetic matrix metalloproteinase-sensitive hydrogels for the conduction of tissue regeneration: engineering cell-invasion characteristics," Proc Natl Acad Sci U S A 100(9):5413-8. (Apr. 29, 2003). Epub Apr. 9, 2003.
Martino et al., "Controlling integrin specificity and stem cell differentiation in 2D and 3D environments through regulation of fibronectin domain stability," Biomaterials 30(6):1089-97 (Feb. 2009). Epub Nov. 22, 2008.
Martino et al., "Engineering the growth factor microenvironment with fibronectin domains to Promote Wound and Bone Tissue Healing," Sci. Trans. Med. 3(100);100ra89, 10 pages (Sep. 14, 2011).
McDonald et al., "Fabrication of microfluidic systems in poly(dimethylsiloxane)," Electrophoresis 21 :27-40 (Jan. 1, 2000). First published: Dec. 29, 1999.
Pastor et al., "CD28 aptamers as powerful immune response modulators," Mol Ther Nucleic Acids 2:e98, 9 pages (Jun. 11, 2013).
Petka et al., "Reversible hydrogels from self-assembling artificial proteins," Science 281(5375):389-392 (Jul. 1998).
Poirier et al., "CD28-specific immunomodulating antibodies: what can be learned from experimental models?" American Journal of Transplantation 12(7): 1682-1690 (Jul. 2012). Epub Apr. 4, 2012.
Porto, "Polymer Biocompatibility," Polymerization, Dr. Ailton De Souza Gomes (Ed.), 17 pages (2012).
Qui et al., "Apoptosis of multiple myeloma cells induced by agonist monoclonal antibody against human CD28," Cell Immunol. 236(1-2): 154-60 (Jul.-Aug. 2005). Epub 2005 Sep. 26, 2005.
Riley et al., Human T regulatory cell therapy: take a billion or so and call me in the morning, Immunity 30(5):656-65. (May 2009).
Sugiura et al., "Effect of Channel Structure on Microchannel Emulsification," Languimir 18(15): 5708-5712 (Jun. 22, 2002).
Weinkove et al., "Selecting costimulatory domains for chimeric antigen receptors: functional and clinical considerations," Clin Transl Immunology 8(5):e1049, p. 1-14 (May 11, 2019).
Xu et al., "Hyaluronic Acid-Based Hydrogels: From a Natural Polysaccharide to Complex Networks," Soft Matter. 8(12):3280-3294 (Mar. 2012).
Yadav and Redmond, "Current Clinical Trial Landscape of OX40 Agonists," Curr Oncol Rep. 24(7):951-960 (Jul. 2022).
Yang et al., "IDBD: Infectious Disease Biomarker Database," Nucleic Acid Res. 36:D455-D460 (Jan. 2008). Published online Nov. 3, 2007.
Zhang et al., "Protein engineering with unnatural amino acids," Current Opinion in Structural Biology 23(4):581-587 (Aug. 2013).

* cited by examiner

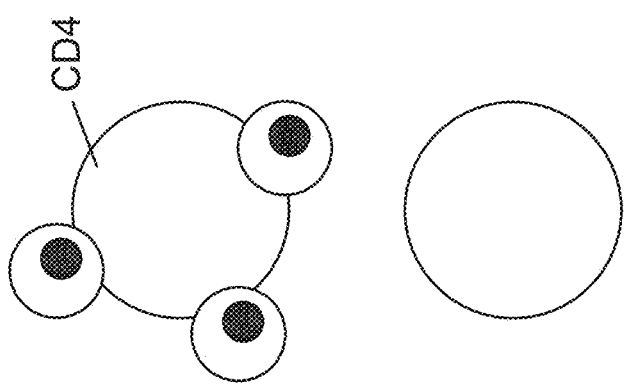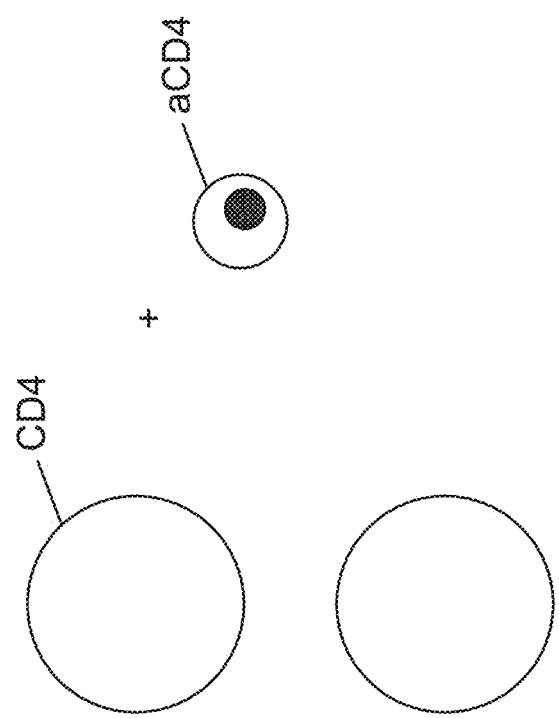
FIG. 4D

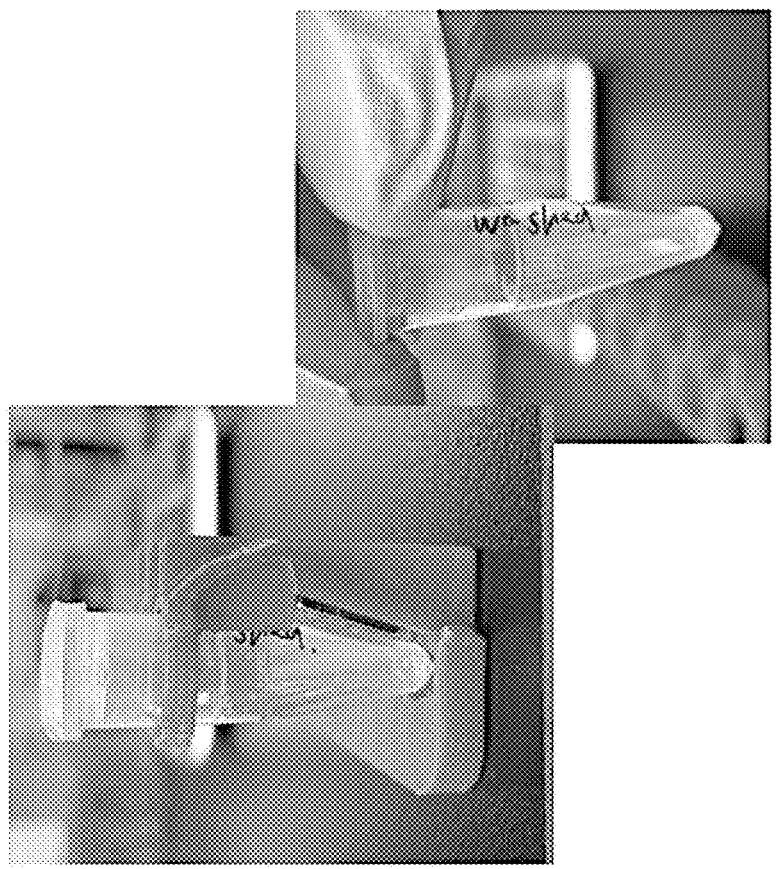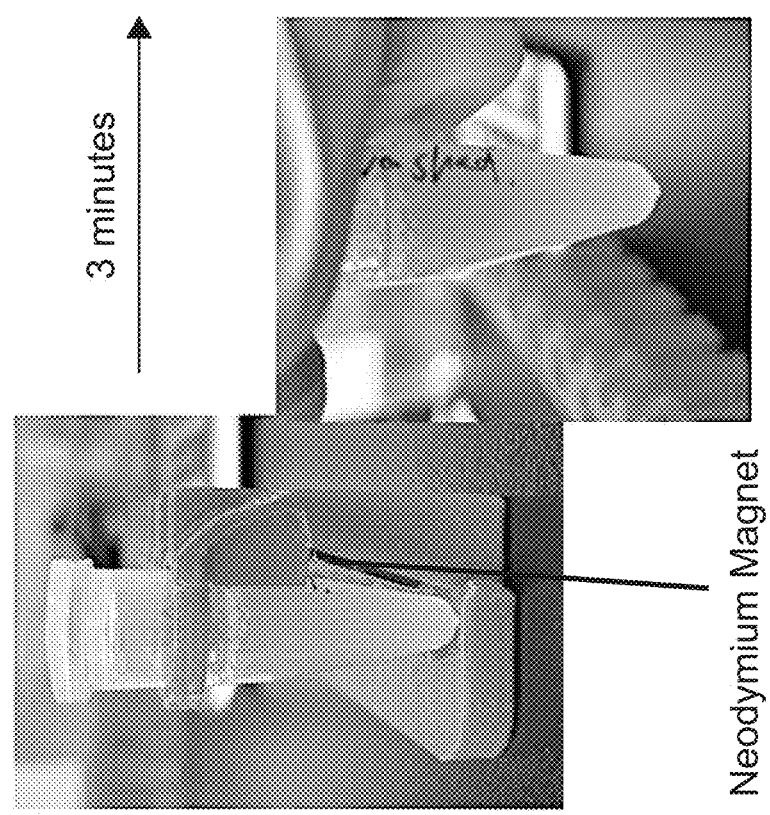
FIG. 4E

| Particle Size | 15 - 25 microns |
| --- | --- |
| Activation | IL-15, IL-21, and CD137 - (One or more activation markers can be conjugated to a same bead) |
| Composition | Biocompatible and biodegradable (< 7 day degradation) |
| Concentration | 1:5 dilution |

- Synthetic feeder cells that replicate engineered K562 in supporting NK expansion

| Particle Size | 10 – 20 micron |
|---|---|
| Cell activation | anti-CD3 (clone OKT3) anti-CD28 (clone 15E8) |
| Composition | • Biocompatible and biodegradable (< 3 day degradation)<br>• Customize hydrogel elasticity to mimic cell-to-cell interaction |
| Concentration | 1:100 dilution |

FIG. 6B

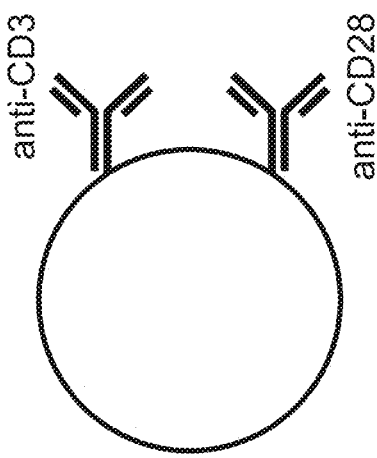

- Biocompatible and biodegradable hydrogel
- Elasticity to more accurately mimic cell-to-cell synapse (ligand-receptor) interaction

FIG. 6A

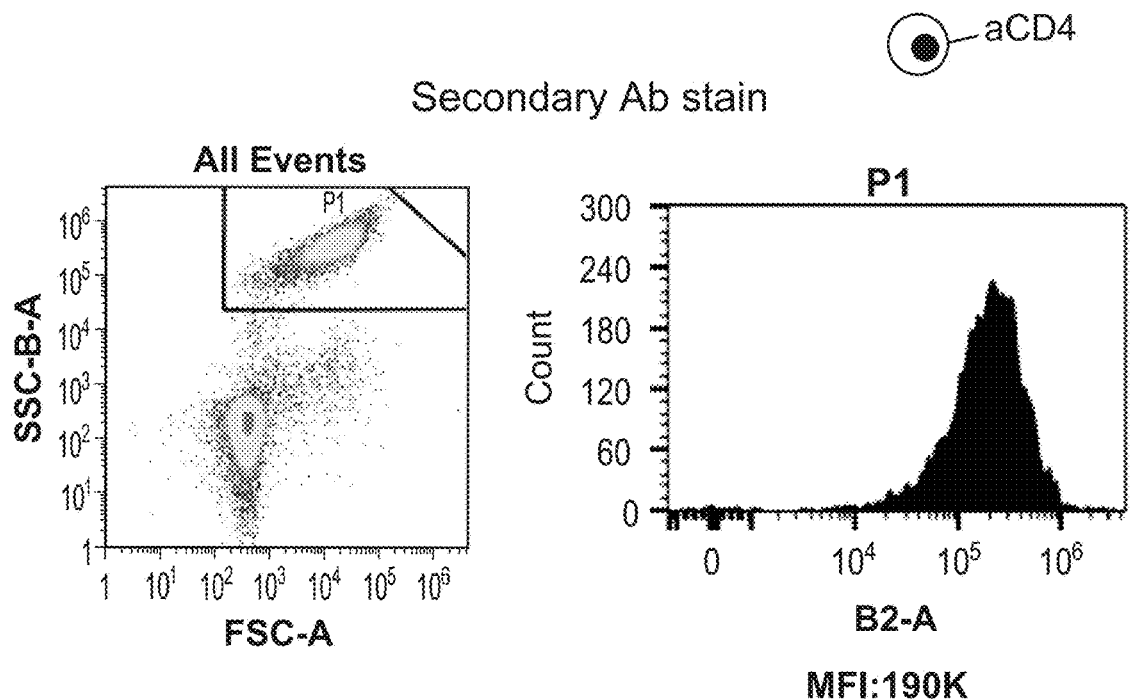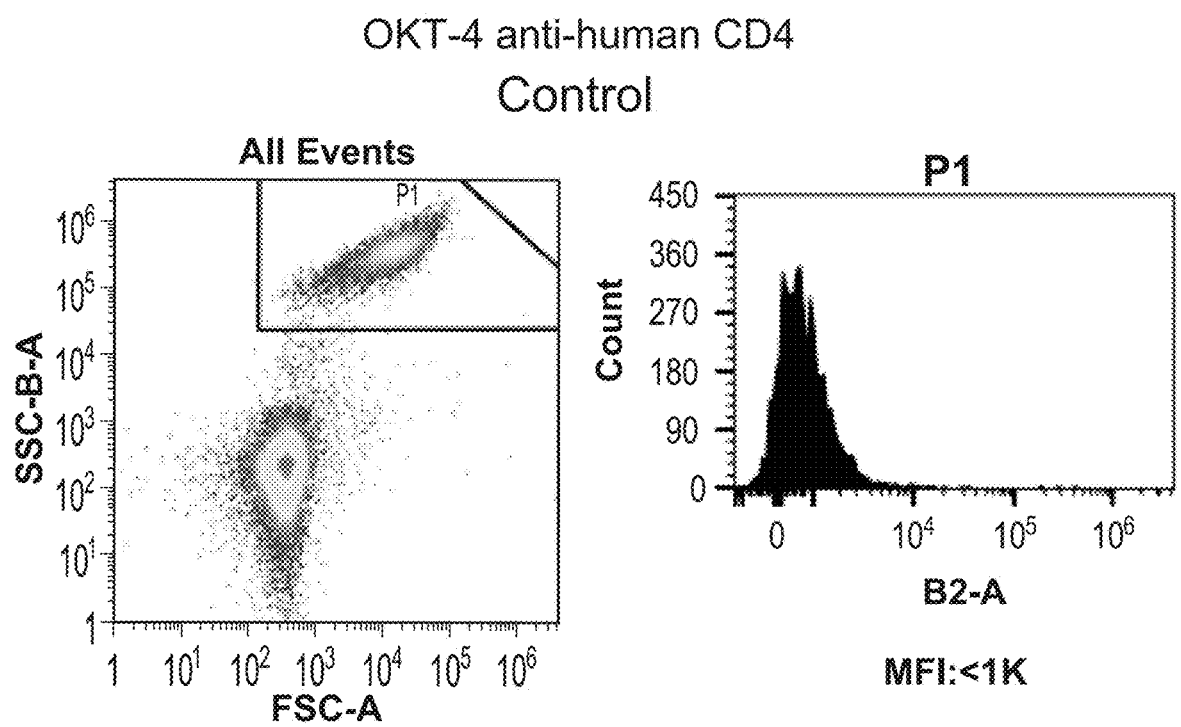
FIG. 7A

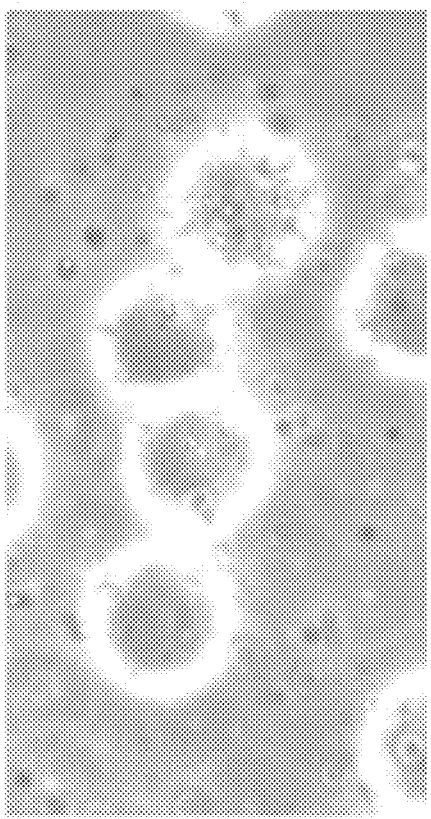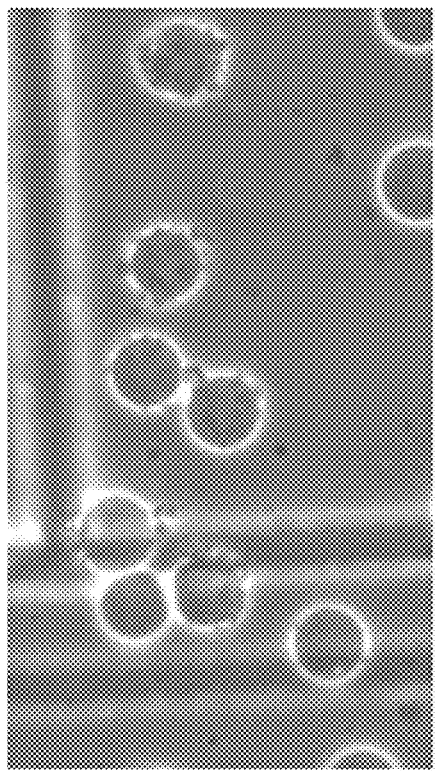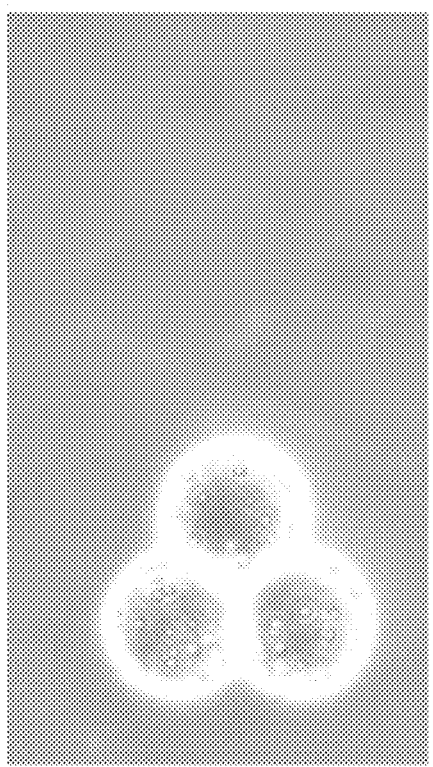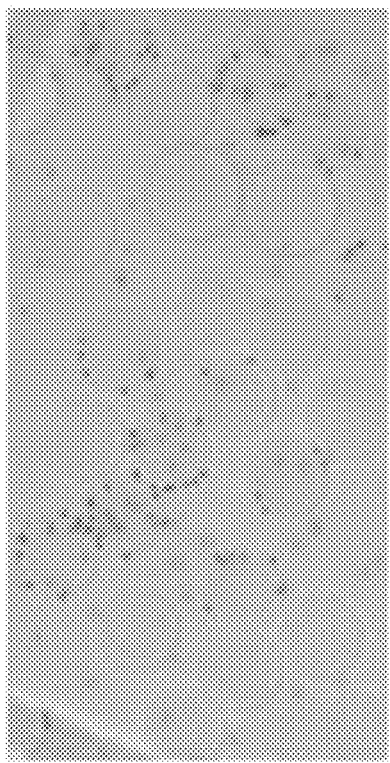
FIG. 7B

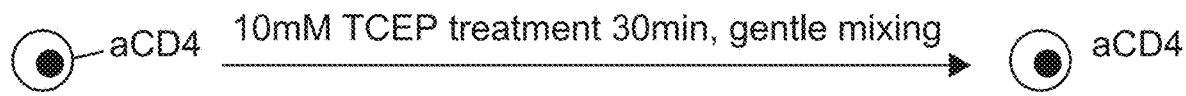
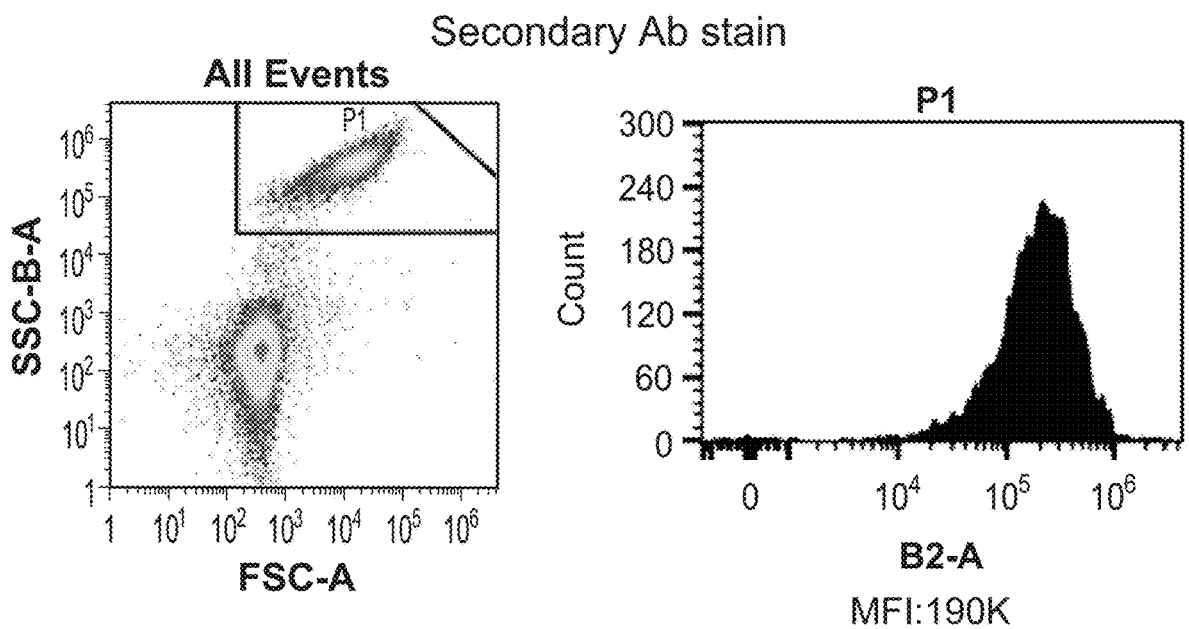
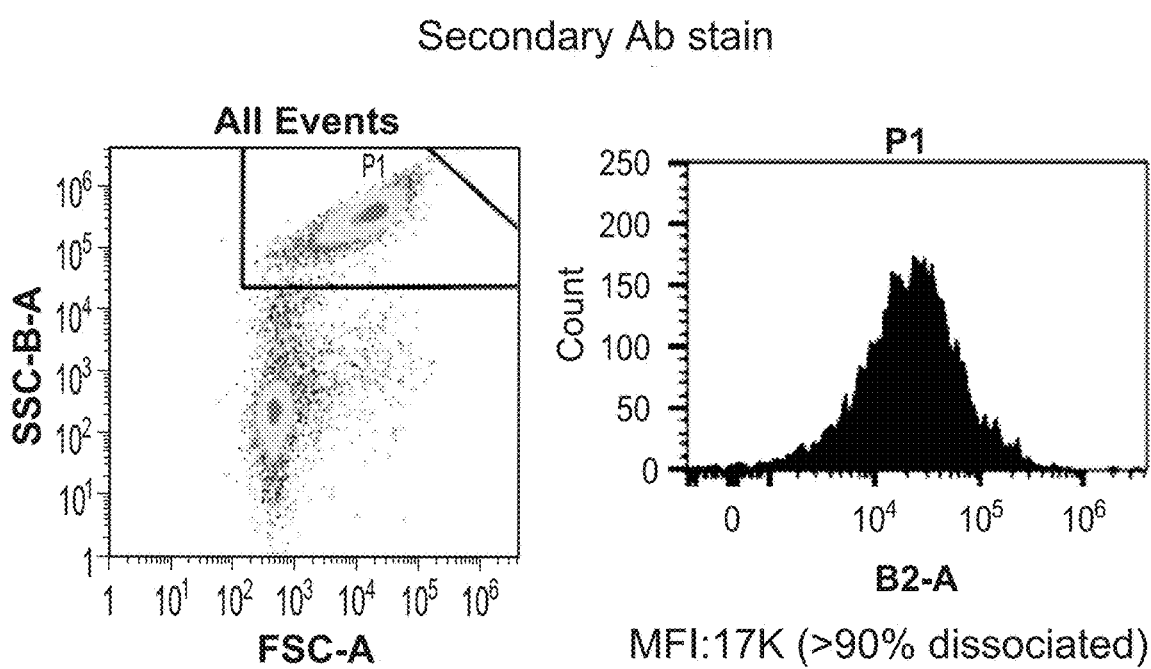
Horse Anti-Mouse IgG Antibody (H+L),
DyLight™ 488 DI-2488-1.5
Vector Laboratories
FIG. 8A

HYDROGEL PARTICLES AS FEEDER CELLS AND AS SYNTHETIC ANTIGEN PRESENTING CELLS

CROSS-REFERENCE TO RELATED APPLICATIONS

This application is a bypass continuation of International Patent Application No. PCT/US2022/048283, filed on Oct. 28, 2022, which claims the benefit of U.S. Provisional Patent Application No. 63/273,741, filed Oct. 29, 2021, U.S. Provisional Patent Application No. 63/320,009, filed Mar. 15, 2022, U.S. Provisional Patent Application No. 63/274,316, filed Nov. 1, 2021, and U.S. Provisional Patent Application No. 63/320,016, filed Mar. 15, 2022, each of which is incorporated by reference herein in its entirety for all purposes.

FIELD OF THE DISCLOSURE

The present disclosure relates to one or more of hydrogel particles as feeder cells, functionalized hydrogel particles, and the like.

BACKGROUND

Cultures of growth-arrested feeder cells have been used for years to promote cell proliferation, particularly with low-density inocula. Feeder cells are incubated with the target cell and provide extracellular secretions to help the target cell proliferate. This differs from a coculture system because only one cell type, the target cell, is capable of proliferation.

However, while the origin of feeder cells may not, be important for solely in vitro uses, when clinical uses are intended, feeder cells are implicated with safety issues. For example, the use of animal feeder cells like 3T3 murine fibroblasts runs the risk of cross-transfer of animal pathogens from the animal feeder, matrix, or conditioned medium to the culture, compromising later clinical applications. Moreover, mouse feeder layers express N-glycolylneuraminic acid (Neu5Gc), a nonhuman sialic acid. Human cells cannot produce Neu5Gc from Neu5Ac, but can incorporate Neu5Gc from the animal feeder layer or from the culture medium, leading to an immune response mediated by circulating antibodies against Neu5Gc present in most healthy humans. Xenogeneic feeder cells have also a risk of contamination, as feeder cells also detach from the surface when target cells are digested from culture flasks. Contamination with feeder cells can cause severe problems when target cells are used for clinical purposes.

Immunotherapy involving priming and expansion of T lymphocytes (T cells) is a promising treatment for the treatment of cancer and infectious disease. Currently, studies use adoptive transfer of T cells stimulated in vitro on autologous dendritic cells (DCs), virally infected B cells, and/or allogenic feeder cells cloned and injected with expanded T cells. However, these uses requires billions of T cells, and co-culturing the T cells with other cell types may induce undesirable immune reactions or the introduction of viruses when the expanded T cells are administered to a patient.

BRIEF SUMMARY

The present disclosure provides hydrogel particles that function as synthetic feeder cells to stimulate the maintenance and or proliferation of target cells in culture. In some aspects of the disclosure, the hydrogel particle comprises one or more cytokines or fragments thereof that stimulate target cell proliferation.

In some aspects, the present disclosure provides a feeder hydrogel particle of e.g., FIG. 2.

In some aspects, the present disclosure provides a method of supporting cell growth or increasing cell proliferation and/or activation of a target cell in culture comprising culturing the target cell with one or more feeder hydrogel particles comprising one or more molecules that support cell growth or increase target cell proliferation and/or activation.

In some aspects, the present disclosure provides a feeder hydrogel particle comprising one or more molecules that support cell growth or increase target cell proliferation and/or activation.

In some aspects, the present disclosure provides a composition comprising a culture of target cells and one or more feeder hydrogel particles comprising one or more molecules that support cell growth or increase target cell proliferation and/or activation.

In some embodiments, the target cell is a stem cell or a lymphocyte. In some embodiments, the lymphocyte is T cell, a natural killer cell, or both.

In some embodiments, the feeder hydrogel particle comprises one or more interleukin and/or members of the tumor necrosis factor superfamily. In some embodiments, the feeder hydrogel particle comprises one or more of IL-2, IL-7, IL-15, IL-21, CD137L, and CD137. In some embodiments, the feeder hydrogel particle comprises IL-2, IL-7, IL-15, IL-21, CD137L, and CD137.

In some embodiments, the present disclosure provides hydrogel particles that can function as an antigen presenting cell (APC) mimic, as shown in FIG. 3. In some embodiments, the hydrogel particle is capable of T cell growth, division, differentiation, expansion, proliferation, activity, viability, exhaustion, anergy, quiescence, apoptosis, in various situations (e.g., in vitro, ex vivo, or in vivo). In some embodiments, the hydrogel particle is useful to promote cell death.

In some embodiments, the present disclosure provides an APC hydrogel particle of e.g., FIG. 3, wherein the APC hydrogel comprises a hydrogel matrix with antigens on a surface thereof.

In some embodiments, the present disclosure provides a method of inducing proliferation, expansion, and/or activation of a T cell in culture comprising culturing the T cell with one or more APC hydrogel particles comprising one or more molecules that induce proliferation, expansion, and/or activation of a T cell.

In some embodiments, the present disclosure provides an APC hydrogel particle comprising one or more molecules that induce proliferation, expansion, and/or stimulation of a T cell.

In some embodiments, the present disclosure provides a composition comprising a culture of T cells and one or more APC hydrogel particles comprising one or more molecules that induce T cell proliferation, expansion, and/or activation.

In some embodiments, the T cell is a cytotoxic T cell. In some embodiments, the T cell is a CAR T cell.

In some embodiments, the APC hydrogel particle comprises one or more T cell stimulatory molecules. In some embodiments, the APC hydrogel particle comprises one or more T cell costimulatory molecules. In some embodiments, the APC hydrogel particle comprises one or more T cell stimulatory molecules and one or more T cell costimulatory molecules.

In some embodiments, the APC hydrogel particle comprises an antibody or fragment thereof that specifically binds one or more T cell stimulatory molecules. In some embodiments, the APC hydrogel particle comprises an antibody or fragment thereof that specifically binds one or more T cell costimulatory molecules. In some embodiments, the APC hydrogel particle comprises an antibody or fragment thereof that specifically binds one or more T cell stimulatory molecules and an antibody or fragment thereof that specifically binds one or more T cell costimulatory molecules. In some embodiments, the APC hydrogel particle comprises an anti-CD3 antibody or fragment thereof. In some embodiments, the APC hydrogel particle comprises an anti-CD28 antibody or fragment thereof. In some embodiments, the APC hydrogel particle comprises an anti-CD3 antibody or fragment thereof and an anti-CD28 antibody or fragment thereto.

In some embodiments, the feeder or APC hydrogel particle is composed of a monomer selected from hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methacrylate, methacrylic acid, sodium methacrylate, glycerol methacrylate, hydroxypropyl methacrylate, hydroxybutyl methacrylate, phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide N-(4-methylphenyl) methyl acrylamide, N-1-naphthyl acrylamide, N-4-nitrophenyl acrylamide, N-(2-phenylethyl)acrylamide, N-triphenylmethyl acrylamide, N-(4-hydroxyphenyl)acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-(2-phenylethyl)methacrylamide, N-triphenylmethyl methacrylamide, N-(4-hydroxyphenyl)methacrylamide, N,N-methylphenyl methacrylamide, N,N'-phenyl phenylethyl methacrylamide, N-vinylcarbazole, 4-vinylpyridine, 2-vinylpyridine, or a combination thereof.

In some embodiments, the monomer is a biodegradable monomer. In some embodiments, the biodegradable monomer is a monosaccharide, disaccharide, polysaccharide, peptide, protein, or protein domain. In some embodiments, the biodegradable monomer is a protein or protein domain comprising at least one non-natural amino acid. In some embodiments, biodegradable monomer is a structural polysaccharide. In some embodiments, the biodegradable monomer is agar, agarose, alginic acid, alguronic acid, alpha glucan, amylopectin, amylose, arabinoxylan, beta-glucan, callose, capsullan, carrageenan polysaccharide, cellodextrin, cellulin, cellulose, chitin, chitosan, chrysolaminarin, curdlan, cyclodextrin, alpha-cyclodextrin, dextrin, dextran, ficoll, fructan, fucoidan, galactoglucomannan, galactomannan, galactose amino galactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage glucan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, or a combination thereof. In some embodiments, the biodegradable monomer is chitosan or hyaluronan. In some embodiments, the protein is a structural protein, a domain thereof, or a combination thereof. In some embodiments, the protein is a proteoglycan, a domain thereof, or a combination thereof. In some embodiments, the protein is an extracellular matrix component. In some embodiments, the proteoglycan is decorin, biglycan, testican, bikunin, fibromodulin, lumican, a domain thereof, or a combination thereof. In some embodiments, the protein is collagen, elastin or a proteoglycan. In some embodiments, the protein is collagen. In some embodiments, the collagen is collagen type I, collagen type II, collagen type III, a domain thereof or a combination thereof.

In some embodiments, the monomer is functionalized. In some embodiments, the monomer is functionalized with acrylate or acrylamide.

In some embodiments, the monomer is bifunctional.

In some embodiments, the hydrogel particle is functionalized on at least one surface.

In some embodiments, components of the feeder cells such as cytokines can be incorporated into the matrix and some others on the cell surface so the feeder cells achieve at least two effects: a) a physical anchor for the target and b) cytokine A and cytokine B support,—at different times, post activation by encapsulating cytokine A and cytokine B in two different materials with different rates of dissolution.

In some embodiments, a mixture of feeder cells and two different base components can be sued. For instance, feeder cells A with PLGA and feeder cells B with hydrogel can be used such that the need for re-feeding the NK cells could be reduced (because the feeder cells persist in culture for longer.)

BRIEF DESCRIPTION OF THE DRAWINGS

FIG. 4A through FIG. 4D are schematics related to magnetically-functionalized hydrogel particles, according to embodiments of the present disclosure.

FIG. 4E provides illustrations of aspects of magnetically-functionalized hydrogel particles, according to embodiments of the present disclosure.

FIG. 6A and FIG. 6B relate to antigen presenting-hydrogel particles, according to embodiments of the present disclosure.

FIG. 7A shows staining of anti-CD4-conjugated magnetic nanoparticle containing hydrogels with a fluorescently labeled secondary antibody, which demonstrate an mean fluorescence intensity (MFI) of 190k, indicating that the hydrogels contain a significant amount of bound anti-CD4.

FIG. 7B shows capture beads bound specifically with hydrogel lymphocyte (Lympho) mimics Top panels show positive control interaction between streptavidin and biotin hydrogels. Bottom panels show Anti-CD4 beads with CD4+ hydrogels.

FIG. 8A shows cleavage between bound antibody and hydrogel beads with (tris(2-carboxyethyl)phosphine) (TCEP) to allow purification of positively selected cells.

DETAILED DESCRIPTION OF THE INVENTION

Definitions

Figure 1:
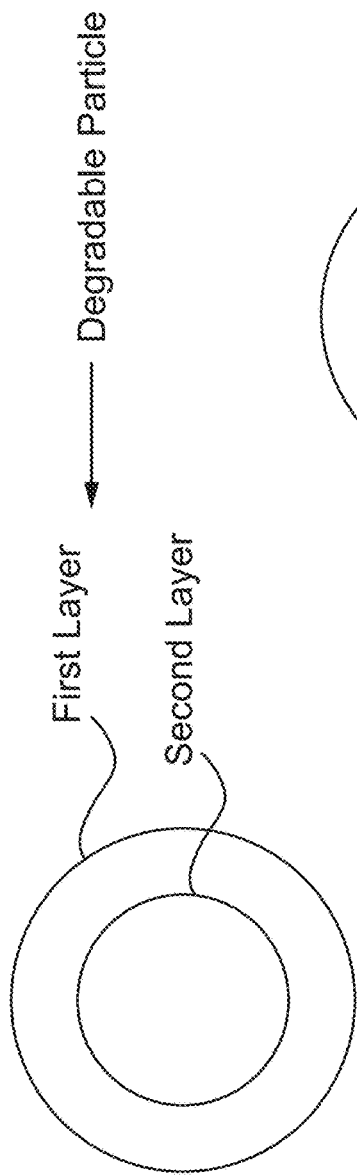
FIG. 1 is a schematic of a degradable hydrogel particle, according to embodiments of the present disclosure.

The indefinite articles "a" and "an" and the definite article "the" are intended to include both the singular and the plural, unless the context in which they are used clearly indicates otherwise. "At least one" and "one or more" are used interchangeably to mean that the article may include one or more than one of the listed elements.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

"Substantially similar," as used herein, denotes at least 40% similar, at least 50% similar, at least 60% similar, at least 70% similar, at least 80% similar, at least 90% similar, at least 95% similar, at least 96% similar, at least 97% similar, at least 98% similar or at least 99% similar.

Unless otherwise indicated, it is to be understood that all numbers expressing quantities, ratios, and numerical properties of ingredients, reaction conditions, and so forth, used in the specification and claims are contemplated to be able to be modified in all instances by the term "about".

As used herein, the term "contacting" (i.e., contacting a cell e.g., a differentiable cell, with a compound) is intended to include incubating the compound and the cell together in vitro (e.g., adding the compound to cells in culture). It is understood that the cells contacted with the defined medium can be further treated with a cell differentiation environment to stabilize the cells, or to differentiate the cells.

As used herein, the term "stabilize," when used in reference to the differentiation state of a cell or culture of cells, indicates that the cells will continue to proliferate over multiple passages in culture, and preferably indefinitely in culture, where most, if not all, of the cells in the culture are of the same differentiation state. In addition, when the stabilized cells divide, the division typically yields cells of the same cell type or yields cells of the same differentiation state. A stabilized cell or cell population in general, does not further differentiate or de-differentiate if the cell culture conditions are not altered and the cells continue to be passaged and are not overgrown. In one embodiment, the cell that is stabilized is capable of proliferation in the stable state indefinitely, or for at least more than 2 passages. In a more specific embodiment, the cells are stable for more than 3 passages, 4 passages, 5 passages, 6 passages, 7 passages, 8 passages, 9 passages, more than 10 passages, more than 15 passages, more than 20 passages, more than 25 passages, or more than 30 passages. In one embodiment, the cell is stable for greater than approximately 1 month, 2 months, 3 months, 4 months, 5 months, 6 months, 7 months, 8 months, 9 months, 10 months, or 11 months of continuous passaging. In another embodiment, the cell is stable for greater than approximately 1 year of continuous passaging. In one embodiment, stem cells are maintained in culture in a pluripotent state by routine passage in the defined medium until it is desired that they be differentiated. As used herein, the term "proliferate" refers to an increase in the number cells in a cell culture.

Hence, as used herein, the term "growth environment" is an environment in which stem cells (e. g., primate embryonic stem cells) will proliferate in vitro. Features of the environment include the medium in which the cells are cultured, and a supporting structure (such as a substrate on a solid surface) if present.

A "defined" medium refers to a biochemically defined formulation comprised solely of the biochemically-defined constituents. A defined medium may include solely constituents having known chemical compositions. A defined medium may also include constituents that are derived from known sources. For example, a defined medium may also include factors and other compositions secreted from known tissues or cells; however, the defined medium will not include the conditioned medium from a culture of such cells. Thus, a "defined medium" may, if indicated, include particular compounds added to form the culture medium.

As used herein, the term "basal medium" refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cells' survival. These are compounds that the cells themselves cannot synthesize, due to the absence of one or more of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. A number of base media are known in the art of mammalian cell culture, such as Dulbecco's Modified Eagle Media (DMEM), Knockout-DMEM (KO-DMEM), and DMEM/F12, although any base medium that supports the growth of primate embryonic stem cells in a substantially undifferentiated state can be employed. A "basal medium" as described herein also refers to the basal medium described in PCT/US2007/062755, filed Jun. 13, 2007, which is herein incorporated in its entirety.

The present disclosure can be used on any appropriate detection or analysis platform, including, without limitation, imaging (e.g., a microscope, a scanner, or the like), flow cytometry, or other immunodetection methods (e.g., an ELISA assay), electrophoresis, omic analysis (genomics, glycomics, proteomics, lipidomics analysis), molecular analysis (q-PCR etc.), or the like. Analysis, such as imaging or detecting, can be performed in fluorescence, bright field, dark field, or immunohistochemical (e.g. chromogenic stains).

Hydrogel Particles

In one aspect, a composition comprising a plurality of hydrogel particles is provided, wherein the individual hydrogel particles of the plurality each has one or more properties substantially similar to one or more properties of a target cell. Each of the individual hydrogel particles of the plurality independently comprises a hydrogel which is synthesized by polymerizing one or more monomers, i.e., to form a homopolymer or copolymer. As discussed further below, the use of bifunctional monomers allows for the further derivatization of hydrogels, e.g., with cell surface markers or epitope binding fragments thereof, or a combination thereof. Methods for tuning the properties of a hydrogel are described herein. The ability to adjust a range of parameters including hydrogel components and concentration of the same allows for the ability to tune a particle to mimic a wide range of cells, for example one of the cell types described herein.

As provided above, in one aspect, the present disclosure provides individual hydrogel particles each having one or more properties substantially similar to one or more properties of a target cell (e.g. size or elasticity).

The present disclosure is based in part on the unexpected discovery that one or more properties of a hydrogel particle can be independently modulated by altering the composition of the hydrogel particle, for example, by altering the amount of initial monomer (or co-monomer) in the composition, by altering the surface functionalization, by altering the amount of a polymerization initiator or by altering the amount of crosslinker. Furthermore, properties of hydrogel particles can be tuned without having a substantial effect on density of the particle. This is a surprising and useful feature, as hydrogel particles that serve as surrogates for cells require a minimal density in order to function appropriately.

In another aspect, a method for producing a hydrogel particle is provided, wherein the hydrogel particle has one or more properties substantially similar to the properties of one or more target cells. In one embodiment, the hydrogel particle has pre-determined properties.

Figure 2:
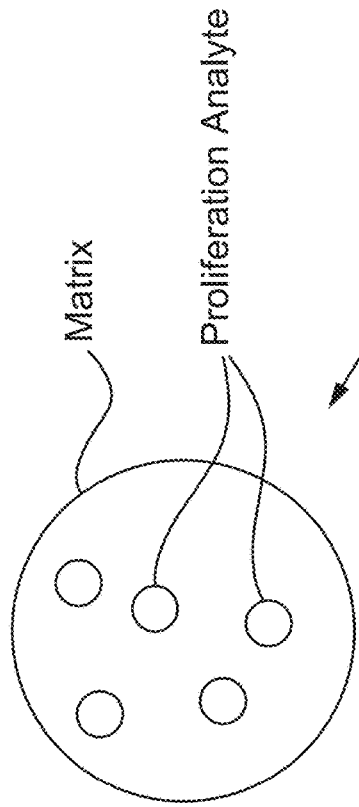
FIG. 2 is a schematic of a hydrogel particle as a feeder cell, according to embodiments of the present disclosure.
Figure 3:
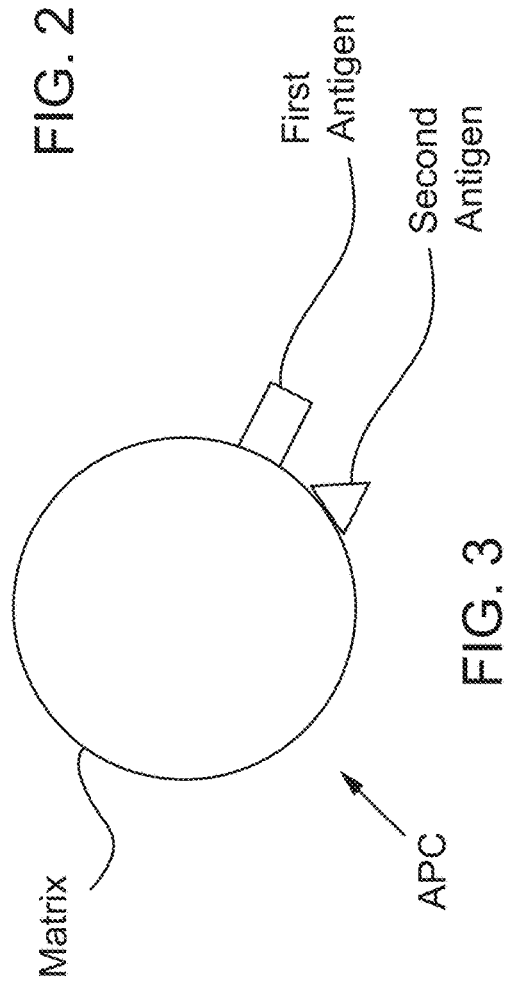
FIG. 3 is a schematic of an antigen presenting-hydrogel particle, according to embodiments of the present disclosure.

In another aspect, a method for producing a synthetic feeder cell, as shown in FIG. 2, comprising one or more hydrogel particles is provided. In some embodiments, the hydrogel particle comprises one or more factors that stimulate cell growth and/or cell proliferation.

As provided above, in one aspect of the present disclosure, compositions comprising a plurality of hydrogel particles are provided. A hydrogel is a material comprising a macromolecular three-dimensional network that allows it to swell when in the presence of water, to shrink in the absence of (or by reduction of the amount of) water, but not dissolve in water. The swelling, i.e., the absorption of water, is a consequence of the presence of hydrophilic functional groups attached to or dispersed within the macromolecular network. Crosslinks between adjacent macromolecules result in the aqueous insolubility of these hydrogels. The cross-links may be due to chemical (i.e., covalent) or physical (i.e., VanDer Waal forces, hydrogen-bonding, ionic forces, etc.) bonds. Synthetically prepared hydrogels can be prepared by polymerizing a monomeric material to form a backbone and cross-linking the backbone with a crosslinking agent. As referred to herein, the term "hydrogel" refers to the macromolecular material whether dehydrated or in a hydrated state. A characteristic of a hydrogel that is of particular value is that the material retains the general shape, whether dehydrated or hydrated. Thus, if the hydrogel has an approximately spherical shape in the dehydrated condition, it will be spherical in the hydrated condition.

In one embodiment, a hydrogel particle disclosed herein comprises greater than about 30%, greater than about 40%, greater than about 50%, greater than about 55%, greater than about 60%, greater than about 65%, greater than about 70%, greater than about 75%, greater than about 80%, greater than about 85%, greater than about 90%, or greater than about 95% water. In another embodiment, a hydrogel particle has a water content of about 10 percent by weight to about 95 percent by weight, or about 20 percent by weight to about 95 percent by weight, or about 30 percent by weight to about 95 percent by weight, or about 40 percent by weight to about 95 percent by weight, or about 50 percent by weight to about 95 percent by weight, or about 60 percent by weight to about 95 percent by weight, or about 70 percent by weight to about 95 percent by weight, or about 80 percent by weight to about 95 percent by weight.

The hydrogels provided herein, in the form of particles, are synthesized by polymerizing one or more of the monomers provided herein. The synthesis is carried out to form individual hydrogel particles. The monomeric material (monomer) in one embodiment is polymerized to form a homopolymer. However, in some embodiments copolymers of different monomeric units (i.e., co-monomers) are synthesized and used in the methods provided herein. The monomer or co-monomers used in the methods and compositions described herein, in some embodiments, is a bifunctional monomer or includes a bifunctional monomer (where co-monomers are employed). In some embodiments, the hydrogel is synthesized in the presence of a crosslinker. In further embodiments, embodiment, the hydrogel is synthesized in the presence of a polymerization initiator.

The amount of monomer can be varied by the user of the disclosure, for example to obtain a particular property that is substantially similar to that of a target cell. In one embodiment, the monomeric component(s) (i.e., monomer, co-monomer, bifunctional monomer, or a combination thereof, for example, bis/acrylamide in various crosslinking ratios, allyl amine or other co-monomers which provide chemical functionality for secondary labeling/conjugation or alginate is present at about 10 percent by weight to about 95 percent weight of the hydrogel. In further embodiments, the monomeric component(s) is present at about 15 percent by weight to about 90 percent weight of the hydrogel, or about 20 percent by weight to about 90 percent weight of the hydrogel.

Examples of various monomers and cross-linking chemistries available for use with the present disclosure are provided in the Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf, the disclosure of which is incorporated by reference in its entirety for all purposes. For example, hydrazine (e.g., with an NHS ester compound) or EDC coupling reactions (e.g., with a maleimide compound) can be used to construct the hydrogels of the disclosure.

In some embodiments, a monomer for use with the hydrogels provided herein is lactic acid, glycolic acid, acrylic acid, 1-hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, a derivatized version thereof, or a combination thereof.

In some embodiments, one or more of the following monomers is used herein to form a hydrogel of the present disclosure: 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methacrylate, methacrylic acid, sodium methacrylate, glycerol methacrylate, hydroxypropyl methacrylate, hydroxybutyl methacrylate or a combination thereof.

In other embodiments, one or more of the following monomers is used herein to form a tunable hydrogel: phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide N-(4-methylphenyl)methyl acrylamide, N-1-naphthyl acrylamide, N-4-nitrophenyl acrylamide, N-(2-phenylethyl)acrylamide, N-triphenylmethyl acrylamide, N-(4-hydroxyphenyl)acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-(2-phenylethyl)methacrylamide, N-triphenylmethyl methacrylamide, N-(4-hydroxyphenyl)methacrylamide, N,N-methylphenyl methacrylamide, N,N'-phenyl phenylethyl methacrylamide, N-vinylcarbazole, 4-vinylpyridine, 2-vinylpyridine, as described in U.S. Pat. No. 6,657,030, which is incorporated by reference in its entirety herein for all purposes.

Both synthetic monomers and bio-monomers can be used in the hydrogels provided herein, to form synthetic hydrogels, bio-hydrogels, or hybrid hydrogels that comprise a synthetic component and a bio-component (e.g., peptide, protein, monosaccharide, disaccharide, polysaccharide, primary amines sulfhydryls, carbonyls, carbohydrates, carboxylic acids present on a biolmolecule). For example, proteins, peptides or carbohydrates can be used as individual monomers to form a hydrogel that includes or does not include a synthetic monomer (or polymer) and in combination with chemically compatible co-monomers and crosslinking chemistries (see for example, the Thermo Scientific Crosslinking Technical Handbook entitled "Easy molecular bonding→crosslinking→technology,"→available→at tools.lifetechnologies.com/content/sfs/brochures/1602163-Crosslinking-Reagents-Handbook.pdf, the disclosure of which is incorporated by reference in its entirety for all purposes). Compatible crosslinking chemistries include, but are not limited to, amines, carboxyls, and other reactive chemical side groups. Representative reactive groups amenable for use in the hydrogels and monomers described herein are provided in Table 1, below.

TABLE 1

Crosslinker reactive groups amenable for bio-monomer conjugation

| Reactivity class | Target functional group | Reactive chemical group |
|---|---|---|
| Amine reactive | —NH2 | NHS ester |
| | | Imidoester |
| | | Penafluorophenyl ester |
| | | Hydroxymethyl phosphine |
| Carboxyl-to-amine reactive | —COOH | Carbodiimide (e.g., EDC) |
| Sulfhydryl-reactive | —SH | Maeleimide |
| | | Haloacetyl (bromo- or iodo-) |
| | | Pyridylisulfide |
| | | Thiosulfonate |
| | | Vinylsulfonate |
| Aldehyde-reactive (oxidized sugars, carbonyls) | —CHO | Hydrazine Alkoxyamine |
| Photo-reactive, i.e., nonselective, random insertion | Random | Diazirine Aryl azide |
| Hydroxyl (nonaqueous)-reactive | —OH | Isocyanate |
| Azide-reactive | —N3 | phosphine |

In general, any form of polymerization chemistry/methods commonly known by those skilled in the art, can be employed to form polymers. In some embodiments, polymerization can be catalyzed by ultraviolet light-induced radical formation and reaction progression. In other embodiments, a hydrogel particle of the disclosure is produced by the polymerization of acrylamide or the polymerization of acrylate. For example, the acrylamide in one embodiment is a polymerizable carbohydrate derivatized acrylamide as described in U.S. Pat. No. 6,107,365, the disclosure of which is incorporated by reference in its entirety for all purposes. As described therein and known to those of ordinary skill in the art, specific attachment of acrylamide groups to sugars is readily adapted to a range of monosaccharides and higher order polysaccharides, e.g., synthetic polysaccharides or polysaccharides derived from natural sources, such as glycoproteins found in serum or tissues.

In some embodiments, an acrylate-functionalized poly(ethylene) glycol monomer is used as a hydrogel monomer. For example, the PEG in one embodiment is an acrylate or acrylamide functionalized PEG.

In some embodiments, a hydrogel particle comprises a monofunctional monomer polymerized with at least one bifunctional monomer. One example includes, but is not limited to, the formation of poly-acrylamide polymers using acrylamide and bis-acrylamide (a bifunctional monomer). In another embodiment, a hydrogel particle provided herein comprises a bifunctional monomer polymerized with a second bifunctional monomer. One example includes, but is not limited to, the formation of polymers with mixed composition comprising compatible chemistries such as acrylamide, bis-acrylamide, and bis-acrylamide structural congeners comprising a wide range of additional chemistries. The range of chemically compatible monomers, bifunctional monomers, and mixed compositions is obvious to those skilled in the art and follows chemical reactivity principles know to those skilled in the art. (reference Thermo handbook and acrylamide polymerization handbook). See, for example, the Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf) and the Polyacrylamide Emulsions Handbook (SNF Floerger, available at snf.com.au/downloads/Emulsion_Handbook_E.pdf), the disclosure of each of which is incorporated by reference in its entirety for all purposes.

In some embodiments, a hydrogel particle provided herein comprises a polymerizable monofunctional monomer and is a monofunctional acrylic monomer. Non-limiting examples of monofunctional acrylic monomers for use herein are acrylamide; methacrylamide; N-alkylacrylamides such as N-ethylacrylamide, N-isopropylacrylamide or N-tertbutylacrylamide; N-alkylmethacrylamides such as N-ethylmethacrylamide or Nisopropylmethacrylamide; N,N-dialkylacrylamides such as N,N-dimethylacrylamide and N,N-diethyl-acrylamide; N-[(dialkylamino)alkyl] acrylamides such as N-[3dimethylamino) propyl]acrylamide or N-[3-(diethylamino)propyl] acrylamide; N-[(dialkylamino) alkyl] methacrylamides such as N-[3-dimethylamino)propyl] methacrylamide or N-[3-(diethylamino) propyl] methacrylamide; (dialkylamino)alkyl acrylates such as 2-(dimethylamino)ethyl acrylate, 2-(dimethylamino)propyl acrylate, or 2-(diethylamino)ethyl acrylates; and (dialkylamino) alkyl methacrylates such as 2-(dimethylamino) ethyl methacrylate.

A bifunctional monomer is any monomer that can polymerize with a monofunctional monomer of the disclosure to form a hydrogel as described herein that further contains a second functional group that can participate in a second reaction, e.g., conjugation of a fluorophore or cell surface receptor (or domain thereof).

In some embodiments, a bifunctional monomer is selected from the group consisting of: allyl amine, allyl alcohol, allyl isothiocyanate, allyl chloride, and allyl maleimide.

A bifunctional monomer can be a bifunctional acrylic monomer. Non-limiting examples of bifunctional acrylic monomers are N,N'-methylenebisacrylamide, N,N'methylene bismethacrylamide, N,N'-ethylene bisacrylamide, N,N'-ethylene bismethacrylamide, N,N'propylenebisacrylamide and N,N'-(1,2-dihydroxyethylene) bisacrylamide.

Higher-order branched chain and linear co-monomers can be substituted in the polymer mix to adjust the refractive index while maintaining polymer density, as described in U.S. Pat. No. 6,657,030, incorporated herein by reference in its entirety for all purposes.

In some embodiments, a hydrogel comprises a molecule that modulates the properties of the hydrogel. Molecules capable of altering properties of a hydrogel are discussed further below.

In some embodiments, an individual hydrogel particle or a plurality thereof comprises a biodegradable polymer as a hydrogel monomer. In one embodiment, the biodegradable polymer is a poly(esters) based on polylactide (PLA), polyglycolide (PGA), polycaprolactone (PCL), poly(lactic-co-glycolic) acid (PLGA) and their copolymers. In some embodiments, the biodegradable polymer is a carbohydrate or a protein, or a combination thereof. For example, in one embodiment, a monosaccharide, disaccharide or polysaccharide, (e.g., glucose, sucrose, or maltodextrin) peptide, protein (or domain thereof) is used as a hydrogel monomer. Other biodegradable polymers include poly(hydroxyalkanoate)s of the PHB-PHV class, additional poly(ester)s, and natural polymers, for example, modified poly(saccharide)s, e.g., starch, cellulose, and chitosan. In other embodiments, the biocompatible polymer is an adhesion protein, cellulose, a carbohydrate, a starch (e.g., maltodextrin, 2-hydroxyethyl starch, alginic acid), a dextran, a lignin, a polyaminoacid, an amino acid, or chitin. Such biodegradable polymers are available commercially, for example, from Sigma Aldrich (St. Louis, MO).

The protein in some embodiments comprises only natural amino acids. However, the present disclosure is not limited thereto. For example, self-assembling artificial proteins and proteins with non-natural amino acids (e.g., those incorporated into non-ribosomal peptides or synthetically introduced via synthetic approaches, see for example, Zhang et al. (2013). Current Opinion in Structural Biology 23, pp. 581-587, the disclosure of which is incorporated by reference in its entirety for all purposes), or protein domains thereof, can also be used as hydrogel monomers. The range of non-natural (unnatural) amino acids that can be incorporated into such compositions is well known to those skilled in the art (Zhang et al. (2013). Current Opinion in Structural Biology 23, pp. 581-587; incorporated by reference in its entirety for all purposes). The biodegradable polymer in one embodiment, is used as a co-monomer, i.e., in a mixture of monomers. The biodegradable polymer in one embodiment is a bifunctional monomer.

The biomonomer, in some embodiments, is functionalized with acrylamide or acrylate. For example, in one embodiment, the polymerizable acrylamide functionalized biomolecule is an acrylamide or acrylate functionalized protein (for example, an acrylamide functionalized collagen or functionalized collagen domain), an acrylamide or acrylate functionalized peptide, or an acrylamide or acrylate functionalized monosaccharide, disaccharide or polysaccharide.

Any monosaccharide, disaccharide or polysaccharide (functionalized or otherwise) can be used as a hydrogel monomer. In some embodiments, an acrylamide or acrylate functionalized monosaccharide, disaccharide or polysaccharide is used as a polymerizable hydrogel monomer. In some embodiments, a structural polysaccharide is used as a polymerizable hydrogel monomer. In further embodiments, the structural polysaccharide is an arabinoxylan, cellulose, chitin or a pectin. In other embodiments, alginic acid (alginate) is used as a polymerizable hydrogel monomer. In yet other embodiments, a glycosaminoglycan (GAG) is used as a polymerizable monomer in the hydrogels provided herein. In further embodiments, the GAG is chondroitin sulfate, dermatan sulfate, keratin sulfate, heparin, heparin sulfate or hyaluronic acid (also referred to in the art as hyaluron or hyaluronate) is used as a polymerizable hydrogel monomer. The additional range of compatible biomonomers and their reactive chemistries are known be individuals skilled in the art and follow general chemical reactivity principles.

An additional range of biocompatible monomers that can be incorporated are known in the art, see, for example the non-degradable biocompatible monomers disclosed in Shastri (2003). Current Pharmaceutical Biotechnology 4, pp. 331-337, incorporated by reference herein in its entirety for all purposes. Other monomers are provided in de Moraes Porto (2012). Polymer Biocompatibility, Polymerization, Dr. Ailton De Souza Gomes (Ed.), ISBN: 978-953-51-0745-3; InTech, DOI: 10.5772/47786; Heller et al. (2010). Journal of Polymer Science Part A: Polymer Chemistry 49, pp. 650-661; Final Report for Biocompatible Materials (2004), The Board of the Biocompatible Materials and the Molecular Engineering in Polymer Science programmes, ISBN 91-631-4985-0, the disclosure of each of which are hereby incorporated by reference in their entirety.

Biocompatible monomers for use with the hydrogels described herein include in one embodiment, ethyleglycol dimethacrylate (EGDMA), 2-hydroxyethyl methacrylate (HEMA), methylmethacrylte (MMA), methacryloxymethyltrimethylsilane (TMS-MA), N-vinyl-2-pyrrolidon (N-VP), styrene, or a combination thereof.

Naturally occurring hydrogels useful in the present disclosure includes various polysaccharides available from natural sources such as plants, algae, fungi, yeasts, marine invertebrates and arthropods. Non-limiting examples include agarose, dextrans, chitin, cellulose-based compounds, starch, derivatized starch, and the like. These generally will have repeating glucose units as a major portion of the polysaccharide backbone. Cross-linking chemistries for such polysaccharides are known in the art, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

Hyaluronan in one embodiment is used as a hydrogel monomer (either as a single monomer or as a co-monomer). Hyaluronan in one embodiment, is functionalized, for example with acrylate or acrylamide. Hyaluronan is a high molecular weight GAG composed of disaccharide repeating units of N-acetylglucosamine and glucuronic acid linked together through alternating β-1,4 and β-1,3 glycosidic bonds. In the human body, hyaluronate is found in several soft connective tissues, including skin, umbilical cord, synovial fluid, and vitreous humor. Accordingly, in one embodiment, where one or more properties of a target cell is desired to be mimicked, in one embodiment, hyaluronan is used as a hydrogel monomer. Methods for fabricating hydrogel particles are described in Xu et al. (2012). Soft Matter. 8, pp. 3280-3294, the disclosure of which is incorporated herein in its entirety for all purposes. As described therein, hyaluronan can be derivatized with various reactive handles depending on the desired cross-linking chemistry and other monomers used to form a hydrogel particle.

In yet other embodiments, chitosan, a linear polysaccharide composed of randomly distributed β-(1-4)-linked D-glucosamine (deacetylated unit) and N-acetyl-D-glucosamine (acetylated unit), is used as a hydrogel monomer (either as a single monomer or as a co-monomer).

Other polysaccharides for use as a hydrogel monomer or co-monomer include but are not limited to, agar, agarose, alginic acid, alguronic acid, alpha glucan, amylopectin, amylose, arabinoxylan, beta-glucan, callose, capsullan, carrageenan polysaccharides (e.g., kappa, iota or lambda class), cellodextrin, cellulin, cellulose, chitin, chitosan, chrysolaminarin, curdlan, cyclodextrin, alpha-cyclodextrin, dextrin, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage glucan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, or a combination thereof. As described throughout, depending on the desired cross-linking chemistry and/or additional co-monomers employed in the hydrogel, the polysaccharide can be further functionalized. For example, one or more of the polysaccharides described herein in one embodiment is functionalized with acrylate or acrylamide.

In some embodiments, an individual hydrogel particle or a plurality thereof comprises a peptide, protein, a protein domain, or a combination thereof as a hydrogel monomer or plurality thereof. In further embodiments, the protein is a structural protein, or a domain thereof, for example, such as silk, elastin, titin or collagen, or a domain thereof. In some embodiments, the protein is an extracellular matrix (ECM) component (e.g., collagen, elastin, proteoglycan, fibrin, lysine, fibronectin). In even further embodiments, the structural protein is collagen. In yet further embodiments, the collagen is collagen type I, collagen type II or collagen type III or a combination thereof. In other embodiments, the hydrogel monomer comprises a proteoglycan. In further embodiments, the proteoglycan is decorin, biglycan, testican, bikunin, fibromodulin, lumican, or a domain thereof.

In other embodiments, an acrylate-functionalized structural protein hydrogel monomer is used as a component of the hydrogel provided herein (e.g., an acrylate functionalized protein or protein domain, for example, silk, elastin, titin, collagen, proteoglycan, or a functionalized domain thereof). In further embodiments, the acrylate functionalized structural protein hydrogel monomer comprises a proteoglycan, e.g., decorin, biglycan, testican, bikunin, fibromodulin, lumican, or a domain thereof.

In some embodiments PEG monomers and oligopeptides can be that mimic extracellular matrix proteins are used in the hydrogels provided herein, for example, with vinyl sulfone-functionalized multiarm PEG, integrin binding peptides and bis-cysteine matrix metalloproteinase peptides as described by Lutolf et al. (2003). Proc. Natl. Acad. Sci. U.S.A. 100, 5413-5418, incorporated by reference in its entirety for all purposes. In this particular embodiment, hydrogels are formed by a Michael-type addition reaction between the di-thiolated oligopeptides and vinyl sulfone groups on the PEG. The range of additional compatible chemistries that can be incorporated here are obvious to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

Other bioactive domains in natural proteins can also be used as a hydrogel monomer or portion thereof. For example, a cell-adhesive integrin binding domain, a controlled release affinity binding domain or a transglutaminase cross-linking domain can be used in the hydrogels provided herein. Details for producing such hydrogels can be found in Martino et al. (2009). Biomaterials 30, 1089; Martino et al. (2011). Sci. Trans. Med. 3, 100ra89; Hu and Messersmith (2003). J. Am. Chem. Soc. 125, 14298, each of which is incorporated by reference in its entirety for all purposes.

In some embodiments, recombinant DNA methods are used to create proteins, designed to gel in response to changes in pH or temperature, for example, by the methods described by Petk et al. (1998). *Science* 281, pp. 389-392, incorporated by reference in its entirety for all purposes. Briefly, the proteins consist of terminal leucine zipper domains flanking a water-soluble polyelectrolyte segment. In near-neutral aqueous solutions, coiled-coil aggregates of the terminal domains form a three-dimensional hydrogel polymer network.

Common cross linking agents that can be used to crosslink the hydrogels provided herein include but are not limited to ethylene glycol dimethacrylate (EGDMA), tetraethylene glycol dimethacrylate, and N,N'-15 methylenebisacrylamide. The range of additional crosslinking chemistries which can be used are obvious to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

In some embodiments, polymerization of a hydrogel is initiated by a persulfate or an equivalent initiator that catalyzes radical formation. The range of compatible initiators are known to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf). The persulfate can be any water-soluble persulfate. Non-limiting examples of water soluble persulfates are ammonium persulfate and alkali metal persulfates. Alkali metals include lithium, sodium and potassium. In some embodiments, the persulfate is ammonium persulfate or potassium persulfate. In further embodiments, polymerization of the hydrogel provided herein is initiated by ammonium persulfate.

Polymerization of a hydrogel can be accelerated by an accelerant which can catalyze the formation of polymerization-labile chemical side groups. The range of possible accelerants is known to those skilled in the art and follow general chemical reactivity principles see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf). The accelerant in one embodiment, is a tertiary amine. The tertiary amine can be any water-soluble tertiary amine. In one embodiment, an accelerant is used in the polymerization reaction and is N,N,N',N'tetramethylethylenediamine, 3-dimethylamino) propionitrile, or N,N,N',N'tetramethylethylenediamine (TEMED). In another embodiment, an accelerant is used in the polymerization reaction and isazobis (isobutyronitrile) (AIBN).

As discussed above, the hydrogel for use in the compositions and methods described herein can include any of the monomeric units and crosslinkers as described herein, and in one aspect, are produced as hydrogel particles by polymerizing droplets (see, e.g., FIG. 2). Microfluidic methods of producing a plurality of droplets, including fluidic and rigidified droplets, are known to those of ordinary skill in the art, and described in US Patent Publication No. 2011/0218123 and U.S. Pat. No. 7,294,503, each incorporated herein by reference in their entireties for all purposes. Such methods provide for a plurality of droplets comprising a first fluid and being substantially surrounded by a second fluid, where the first fluid and the second fluid are substantially immiscible (e.g., droplets comprising an aqueous-based liquid being substantially surrounded by an oil based liquid).

A plurality of fluidic droplets (e.g., prepared using a microfluidic device) may be polydisperse (e.g., having a range of different sizes), or in some cases, the fluidic droplets may be monodisperse or substantially monodisperse, e.g., having a homogenous distribution of diameters, for instance, such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter. The average diameter of a population of droplets, as used herein, refers to the arithmetic average of the diameters of the droplets. Average diameters of the particles can be measured, for example, by light scattering techniques. Average diameters of hydrogel particles in one embodiment, are tailored, for example by varying flow rates of the fluid streams of the first and second fluids within the channel(s) of a microfluidic device, or by varying the volume of the channel(s) of the microfluidic device.

Accordingly, the disclosure provides population of hydrogel particles comprising a plurality of hydrogel particles, wherein the population of hydrogel particles is substantially monodisperse.

The term microfluidic refers to a device, apparatus or system including at least one fluid channel having a cross-sectional dimension of less than 1 mm, and a ratio of length to largest cross-sectional dimension perpendicular to the channel of at least about 3:1. A micro fluidic device comprising a micro fluidic channel is especially well suited to preparing a plurality of mono disperse droplets.

Non-limiting examples of microfluidic systems that may be used with the present disclosure are disclosed in U.S. Patent Application Publication No. 2006/0163385; U.S. Patent Application Publication No. 2005/0172476; U.S. Patent Application Publication No. 2007/000342; International Patent Application Publication No. WO 2006/096571; U.S. Patent Application Publication No. 2007/0054119; U.S. Pat. No. 7,776,927; and International Patent Application Publication No. WO 2006/078841, each incorporated herein by reference in their entireties for all purposes.

Droplet size is related to microfluidic channel size. The micro fluidic channel may be of any size, for example, having a largest dimension perpendicular to fluid flow of less than about 5 mm or 2 mm, or less than about 1 mm, or less than about 500 µm, less than about 200 µm, less than about 100 µm, less than about 60 µm, less than about 50 µm, less than about 40 µm, less than about 30 µm, less than about 25 µm, less than about 10 µm, less than about 3 µm, less than about 1 µm, less than about 300 nm, less than about 100 nm, less than about 30 nm, or less than about 10 nm.

Droplet size can be tuned by adjusting the relative flow rates. In some embodiments, drop diameters are equivalent to the width of the channel, or within about 10%, 15%, 20%, 30%, 40%, 50%, 60%, 70%, 80%, 90%, or 100% the width of the channel.

The dimensions of a hydrogel particle of the disclosure are substantially similar to the droplet from which it was formed. Therefore, in some embodiments, a hydrogel particle has a diameter of less than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or less than 1000 µm in diameter. In some embodiments, a hydrogel particle has a diameter of more than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or greater than 1000 μm in diameter. In one embodiment, a hydrogel particle has a diameter in the range of 5 μm to 100 μm.

In some embodiments, a hydrogel particle of the disclosure is spherical in shape.

In some embodiments, a hydrogel particle of the disclosure does not comprise agarose.

Hydrogel particles in some embodiments, is carried by suspension polymerization, which is also referred to in the art as pearl, bead or granular polymerization (see Elbert (2011). *Acta Biomater.* 7, pp. 31-56, incorporated by reference herein in its entirety for all purposes). In suspension polymerization, the monomer is insoluble in the continuous phase, for example an aqueous monomer solution in a continuous oil phase. In suspension polymerization, polymerization initiation occurs within the monomer-rich droplets and with greater than one radical per droplet at any time. The monomer phase in one embodiment includes a monomer which can be a bifunctional monomer or a plurality of monomer species (co-monomers, which can be a plurality of bifunctional monomers. The monomer phase in one embodiment, includes an initiator and/or a crosslinking agent.

Emulsion polymerization can also be used to form the hydrogel particles described herein. In emulsion polymerization, the monomer has poor solubility in the continuous phase, similar to suspension polymerization, however, polymerization initiation occurs outside the monomer droplets (see Elbert (2011). *Acta Biomater.* 7, pp. 31-56, incorporated by reference herein in its entirety for all purposes). In emulsion polymerization embodiments, the initiator causes chain growth of the monomer (or co-monomers) dissolved in the continuous phase or monomer contained in micelles if surfactants are present.

In other embodiments, hydrogel particles are formed by precipitation polymerization, for example as described in Elbert (2011). *Acta Biomater.* 7, pp. 31-56, incorporated by reference herein in its entirety for all purposes. Precipitation polymerization is a technique that takes advantage of the differences in the solubility of monomer and polymer to produce microparticles. Specifically, it is known that larger polymer chains generally have lower solubility than smaller ones. Accordingly, above a specific molecular weight, phase separation may be favored. Precipitation polymerization initially begins as solution polymerizations in a single phase, homogenous system. Shortly after the start of the polymerization, in one embodiment, a relatively high concentration of polymer chains is present, favoring phase separation by nucleation. As polymerization proceeds, the concentration of polymer chains is low and existing particles capture the chains before nucleation of new particles can occur. Thus, nucleation of particles occurs only for a brief period of time shortly after the start of the reaction, which in one embodiment, results in a narrow size distribution of particles. Additional methods include but are not limited to lithographic particle formation (Helgeson et al. (2011). Curr. Opin. Colloid. Interface Sci. 16, pp. 106-117, incorporated by reference herein in its entirety for all purposes) membrane emulsification (e.g., by the microsieve emulsification technology techniques described by Nanomi B. V. (Netherlands)) and microchannel emulsification (Sugiura et al. (2002). Languimir 18, pp. 5708-5712, incorporated by reference herein in its entirety) and bulk emulsification (SNF Floerger, available at snf.com.au/downloads/ Emulsion_Handbook_E.pdf, incorporated by reference herein in its entirety).

In some embodiments, hydrogel particles are formed within a microfluidic device having two oil channels that focus on a central stream of aqueous monomer solution. In this embodiment, droplets form at the interface of the two channels and central stream to break off droplets in water-in-oil emulsion. Once droplets are formed, in one embodiment, they are stabilized prior to polymerization, for example, by adding a surfactant to the oil phase. However, in another embodiment, droplets are not stabilized prior to polymerization. Polymerization of the monomer in one embodiment is triggered by adding an accelerator (e.g., N,N,N',N'tetramethylethylenediamine) to one or both of the oil channels after initial droplets are formed.

The aqueous monomer solution as provided above can include a single monomer species or a plurality of monomer species. The aqueous monomer solution can include co-monomers, a bifunctional monomer or a combination thereof. In some embodiments, the monomer or plurality of monomers can includes a bifunctional monomer, for example, one of the monomers described above. As described below, co-monomers can be used to modulate particular properties of the hydrogel particle.

In some embodiments, the central stream of aqueous monomer solution comprises a cross-linker, for example, N,N'-bisacrylamide. In further embodiments, the central stream of aqueous monomer solution comprises a cross-linker and an accelerator, in addition to the monomer. In yet further embodiments, the aqueous monomer solution comprises an initiator, for example an oxidizing agent such as ammonium persulfate.

In some embodiments, a bead, plurality of beads, biomolecule, or plurality of biomolecules is embedded (encapsulated) within the hydrogel particle. An encapsulated bead or biomolecule, in some embodiments, is employed to mimic one or more intracellular organelles of a target cell, or a cell after it engulfs a particle. In some embodiments, encapsulating or embedding a bead or biomolecule is accomplished at the time of hydrogel particle formation. For example, beads can be suspended in the appropriate concentration to allow for an average of one bead to be embedded/encapsulated in a single hydrogel particle. The bead suspension can be included, for example, within the aqueous solution of monomer. Similarly, a biomolecule or mixture of biomolecules can be incorporated into the aqueous solution of monomer to encapsulate the biomolecule or biomolecules.

Alternatively, once a hydrogel particle is formed, for example by the methods described above, in some embodiments, it can be further manipulated, for example, by embedding a bead, plurality of beads, biomolecule or plurality of biomolecules within the hydrogel particle.

Accordingly, in one aspect of the disclosure, a hydrogel comprising an embedded substance is provided.

In some embodiments, the embedded substance is an embedded molecule, for example a biomolecule. The biomolecule can be a single species or a plurality of different species. For example, a protein, peptide, carbohydrate, nucleic acid or combination thereof can be encapsulated within a hydrogel particle of the present disclosure. Moreover, different nucleic acid molecules (e.g., of varying sequences or nucleic acid type such as genomic DNA, messenger RNA or DNA-RNA hybrids) can be encapsulated by the hydrogel particle of the present disclosure. These can be comprised of any protein or nucleic acid as both forms of biological material contain labile chemical side-groups (or can be modified by commercial vendors (e.g., Integrated DNA Technology chemical side group modifications). Such side-groups are compatible with reaction chemistries commonly found in co-monomer compositions (e.g. acrylate chemistry, NHS-ester, primary amines, copper catalyzed click chemistry (Sharpless)). The range of possible embedded molecules which contain compatible chemistries is understood by those skilled in the art.

In some embodiments, different subpopulations of hydrogel particles are fabricated, each with a different concentration of biomolecule. In further embodiments, the biomolecule is a nucleic acid, a protein, an intracellular ion such as calcium acid (or other biomolecule of the user's choosing, for example, calcium). In another embodiment, different subpopulations of hydrogel particles are fabricated, each with a different concentration of a drug substance. The drug substance in one embodiment is a biomolecule (i.e., a biologic, antibody, antibody drug conjugate, protein/enzyme, peptide, non-ribosomal peptide, or related molecule) or a small molecule synthetic drug (e.g., Type 14I/III polyketide, non-ribosomal peptide with bioactive properties, or other small molecule entity as generally classified by those skilled in the art).

In this regard, the present disclosure is particularly useful for determining assay resolution where cells are stained for their respective nucleic acid or protein content. In some embodiments, different populations of the hydrogel particles provided herein are encapsulated with known, differing amounts of an intracellular substance, e.g., nucleic acid or protein. Individual hydrogel particles are stained for the intracellular substance and fluorescence is measured via a cytometric device for the individual hydrogels of the various populations. This allows for a generation of a standard curve to establish the sensitivity and dynamic range of the intracellular assay. Once established, a sample can be run through the cytometer to detect target cell(s) if present, and to quantify the amount of intracellular substance in the respective target cell(s). In one embodiment, the embedded substance is an infectious disease biomarker, for example one of the infectious disease biomarkers in the Infectious Disease Biomarker Database (IDBD, see Yang et al. (2008) IDBD: Infectious Disease Biomarker Database. *Nucleic Acid Res.* 36, pp. D455-D460, incorporated by reference in its entirety for all purposes). In a further embodiment, the infectious disease biomarker is a biomarker of gastrointestinal infection, respiratory infection, neurological infection, urogenital infection, viral infection, hemorrhagic fever, zoonosis, arbovirus, antibiotics resistance or bioterrorism. In a further embodiment, the viral infection is an Ebola infection.

In some embodiments, the methods provided herein are used to determine the sensitivity and/or dynamic range of a cellular nucleic acid quantification assay. In this embodiment, a sample is interrogated for cell types within the sample (if present), and amount of cellular nucleic acid within the cell.

In other embodiments, hydrogel particles, in one embodiment, encapsulate known amounts of protein, at various concentrations, and subsequently stained with the appropriate protein antibody. Fluorescence is measured for the various particles to determine the sensitivity and/or dynamic range of the assay. The fluorescence values can then be compared to the values obtained from cells in a sample, to determine whether a target cell is present and whether it contains the intracellular protein, and the amount of the protein.

As provided above, in one aspect of the disclosure, a hydrogel comprising an embedded substance is provided. In some embodiments, the embedded substance is a bead or plurality of beads. In some embodiments, a hydrogel particle is embedded with a single bead. In other embodiments, individual hydrogels the average number of embedded beads in a plurality of hydrogel particles is one.

In some embodiments, a bead with the diameter of about 1 μm to about 3 μm, about 2 μm to about 4 μm or about 3 μm to about 7 μm is embedded in a hydrogel provided herein. For example, in some embodiments, the bead has a diameter of about 3 μm to about 3.5 μm. In further embodiments, the bead is a fluorescent bead. In other embodiments, the bead has a diameter of about 1 μm to about 2.5 μm or about 1.5 μm to about 3 μm. In further embodiments, the bead is a fluorescent bead and can be stained either internally or at its surface. In even further embodiments, the fluorescent bead is stained internally. Without wishing to be bound by theory, it is thought that internal staining insulates the fluorophores from environmental interactions that could cause variable fluorescence output.

In some embodiments, FSC is modulated by adjusting the percentage of monomer present in the composition thereby altering the water content present during hydrogel formation. In some embodiments, where a monomer and co-monomer are employed, the ratio of monomer and co-monomer is adjusted to change the hydrogel particle's properties. For example, the ratio of monomer and co-monomer can be used to adjust the hydrogel particle's elasticity (i.e., Young's Modulus) to be substantially similar to the elasticity of the target cell. The ratio of the monomer and co-monomer can change the Young's Modulus for the hydrogel particle can range from 0.2 kiloPascals (kPa) to 400 kPa, based on the elasticity of the target cell. The elasticity of the hydrogel particle (e.g., softness or firmness) can affect the function of the target cell with which the hydrogel particle interacts.

The FSC of a disclosed hydrogel particle is most meaningfully measured in comparison to that of target cell. In some embodiments, a disclosed hydrogel particle has an FSC within 30%, within 25%, within 20%, within 15%, within 10%, within 5%, or within 1% that of a target cell, as measured by a cytometric device.

FSC is related to particle volume, and thus can be modulated by altering particle diameter, as described herein. Particle diameter in some embodiments is altered to modulate FSC properties of a hydrogel particle. For example, hydrogel particle diameter is increased in one embodiment is altered by harnessing larger microfluidic channels during particle formation.

SSC can be engineered by encapsulating nanoparticles within hydrogels to mimic organelles in a target cell. In some embodiments, a hydrogel particle of the disclosure comprises one or more types of nanoparticles selected from the group consisting of: polymethyl methacrylate (PMMA) nanoparticles, polystyrene (PS) nanoparticles, and silica nanoparticles. Without wishing to be bound by theory, the ability to selectively tune a hydrogel, as described herein, allows for a robust platform to mimic a vast array of cell types.

For example, hydrogel particles can be fabricated and adjusted to tune the capacitance of the particles, e.g., to calibrate coulter counters. In some embodiments, a hydrogel particle's capacitance is adjusted by altering the amount of hydrogel monomer in the composition. For example, polyanaline, polyacetylene; polyphenylene vinylene; polypyrrole (X=NH) and polythiophene (X=S) co-monomers; and polyaniline (X=NH/N) and polyphenylene sulfide (X=S) co-monomer concentrations can all be adjusted to alter capacitance. In some embodiments, the concentration of one or more of these monomers is increased to increase the capacitance of the hydrogel particle.

In some embodiments, a hydrogel particle of the disclosure has material modulus properties (e.g., elasticity) more closely resembling that of a target cell as compared to a polystyrene bead of the same diameter. After the hydrogel particle is formed, one or more of the particle's surfaces can be functionalized, for example, to mimic one or more properties of a target cell. The functionalized hydrogel particle can also include an embedded bead or substance such as a biomolecule, as described above. In some embodiments, one or more hydrogel particles are functionalized with one or more fluorescent dyes, one or more cell surface markers (or epitope binding regions thereof), or a combination thereof. In some embodiments, the hydrogel particle is formed by polymerizing at least one bifunctional monomer and after formation, the hydrogel particle includes one or more functional groups that can be used for further attachment of a cell surface marker, an epitope binding region of a cell surface marker, a fluorescent dye, or combination thereof. The free functional group, in one embodiment, is an amine group, a carboxyl group, a hydroxyl group or a combination thereof. Depending on the functionalization desired, it is to be understood that multiple bifunctional monomers can be used, for example, to functionalize the particle using different chemistries and with different molecules.

A hydrogel particle can be functionalized with any fluorescent dye known in the art, including fluorescent dyes listed in The MolecularProbes® Handbook-A Guide to Fluorescent Probes and Labeling Technologies, incorporated herein by reference in its entirety for all purposes. Functionalization can be mediated by a compound comprising a free amine group, e.g. allylamine, which can be incorporated into a bifunctional monomer used to form the hydrogel, as discussed above.

Non-limiting examples of known fluorescent dyes that can be used to functionalize the surface of a hydrogel particle described herein include: 6-carboxy-4', 5'-dichloro-2', 7'-dimethoxyfluorescein succinimidylester; 5-(and-6)-carboxyeosin; 5-carboxyfluorescein; 6 carboxyfluorescein; 5-(and-6)-carboxyfluorescein; S-carboxyfluorescein-bis-(5-carboxymethoxy-2-nitrobenzyl)ether, -alanine-carboxamide, or succinimidyl ester; 5-carboxyfluoresceinsuccinimidyl ester; 6-carboxyfluorescein succinimidyl ester; 5-(and-6)-carboxyfluorescein succinimidyl ester; 5-(4,6-dichlorotriazinyl) amino fluorescein; 2 ', 7'-difluoro fluorescein; eosin-5-isothiocyanate; erythrosin5-isothiocyanate; 6-(fluorescein-5-carboxamido) hexanoic acid or succinimidyl ester; 6-(fluorescein-5-(and-6)-carboxamido) hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidylester or triethylammonium salt; Oregon Green® 514 carboxylic acid; Oregon Green® 514 carboxylic acid or succinimidyl ester; RhodamineGreen™ carboxylic acid, succinimidyl ester or hydrochloride; Rhodamine Green™ carboxylic acid, trifluoroacetamide or succinimidylester; Rhodamine Green™-X succinimidyl ester or hydrochloride; RhodolGreen™ carboxylic acid, N,O-bis-(trifluoroacetyl) or succinimidylester; bis-(4-carboxypiperidinyl) sulfonerhodamine or di(succinimidylester); 5-(and-6)carboxynaphtho fluorescein, 5-(and-6)carboxynaphthofluorescein succinimidyl ester; 5-carboxyrhodamine 6G hydrochloride; 6-carboxyrhodamine6Ghydrochloride, 5-carboxyrhodamine 6G succinimidyl ester; 6-carboxyrhodamine 6G succinimidyl ester; 5-(and-6)-carboxyrhodamine6G succinimidyl ester; 5-carboxy-2',4',5',7'-tetrabromosulfonefluorescein succinimidyl esteror bis-(diisopropylethylammonium) salt; 5-carboxytetramethylrhodamine; 6-carboxytetramethylrhodamine; 5-(and-6)-carboxytetramethylrhodamine; 5-carboxytetramethylrhodamine succinimidyl ester; 6-carboxytetramethylrhodaminesuccinimidyl ester; 5-(and-6)-carboxytetramethylrhodamine succinimidyl ester; 6-carboxy-X-rhodamine; 5-carboxy-X-rhodamine succinimidyl ester; 6-carboxy-Xrhodamine succinimidyl ester; 5-(and-6)-carboxy-Xrhodaminesuccinimidyl ester; 5-carboxy-X-rhodamine triethylammonium salt; Lissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester; 6-(tetramethylrhodamine-5-(and-6)-carboxamido) hexanoic acid; succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; and X-rhodamine-5-(and-6) isothiocyanate.

Other examples of fluorescent dyes for use with the hydrogel particles described herein include, but are not limited to, BODIPY® dyes commercially available from Invitrogen, including, but not limited to BODIPY® FL; BODIPY® TMR STP ester; BODIPY® TR-X STP ester; BODIPY® 630/650-X STPester; BODIPY® 650/665-X STP ester; 6-dibromo-4, 4-difluoro-5, 7-dimethyl-4-bora-3 a, 4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3 a,4 a-diaza-s-indacene-3-pentanoic acid; 4,4-difluoro-5,7-dimethyl-4-bora3a,4a-diaza-s-indacene-3-pentanoicacid succinimidyl ester; 4,4-difluoro-5,7-dimethyl-4-bora-3 a, 4a-diaza-s-indacene-3propionicacid; 4, 4-difluoro-5, 7-dimethyl-4-bora-3 a, 4adiaza-s-indacene-3-propionicacid succinimidyl ester; 4, 4difluoro-5, 7-dimefhyl-4-bora-3a,4a-diaza-s-indacene-3propionic acid; sulfosuccinimidyl ester or sodium salt; 6-((4,4-difluoro-5, 7-dimethyl-4-bora-3a,4a-diaza-s-indacene-3propionyl)amino) hexanoic acid; 6-((4,4-difluoro-5, 7 dimethyl-4-bora-3a,4a-diaza-s-indacene-3-propionyl) amino) hexanoic acid or succinimidyl ester; N-(4, 4-difluoro 5, 7-dimethyl-4-bora-3 a, 4a-diaza-s-indacene-3-propionyl) cysteic acid, succinimidyl ester or triethylammonium salt; 6-4,4-difluoro-1,3-dimethyl-5-(4-methoxyphenyl)-4-bora3a, 4a4,4-difluoro-5, 7-diphenyl-4-bora-3a,4a-diazasindacene-3-propionicacid; 4, 4-difluoro-5, 7-diphenyl-4-bora3 a, 4a-diaza-s-indacene-3-propionic acid succinimidyl ester; 4, 4-difluoro-5-phenyl-4-bora-3 a, 4a-diaza-s-indacene-3-propionic acid; succinimidyl ester; 6-((4, 4-difluoro-5-phenyl-4 bora-3 a, 4a-diaza-s-indacene-3-propionyl)amino) hexanoicacid or succinimidyl ester; 4,4-difluoro-5-(4-phenyl-1,3butadienyl)-4-bora-3 a, 4a-diaza-s-indacene-3-propionicacid succinimidyl ester; 4, 4-difluoro-5-(2-pyrrolyl)-4-bora-3a,4a-diaza-s-indacene-3-propionic acid succinimidyl ester; 6-4(4,4-difluoro-5-(2-pyrrolyl)-4-bora-3a,4a-diaza-s-indacene-3-yl)styryloxy)acetyl)aminohexanoicacid or succinimidyl ester; 4,4-difluoro-5-styryl-4-bora-3 a, 4a-diaza-s-indacene-3-propionic acid; 4, 4-difluoro-5-styryl-4-bora-3 a, 4a-diaza-sindacene-3-propionic acid; succinimidyl ester; 4,4-difluoro-1,3,5,7-tetramethyl-4-bora-3a,4adiaza-s-indacene-8-propionic acid; 4,4-difluoro-1,3,5,7-tetramethyl-4bora-3a,4a-diaza-sindacene-8-propionicacid succinimidyl ester; 4,4-difluoro-5-(2-thienyl)-4-bora-3a,4a-diaza-sindacene-3-propionicacid succinimidyl ester; 6-(((4-(4, 4-difluoro-5-(2-thienyl)-4- bora-3 a, 4adiazas-indacene-3-yl)phenoxy)acetyl)amino) hexanoic acid or succinimidyl ester; and 6-(((4,4-difluoro-5-(2-thienyl)-4-bora-3a,4a-diaza-s-indacene-3-yl) styryloxy)acetyl) aminohexanoic acid or succinimidyl ester.

Fluorescent dyes for derivatization of the surface of one or more hydrogel particles in one embodiment, include, but are not limited to, Alexa fluor dyes commercially available from Invitrogen, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; and Alexa Fluor® 680 carboxylic acid. In another embodiment, fluorescent dyes for use with the hydrogel particles and methods described herein include cyanine dyes commercially available from Amersham-Pharmacia Biotech, including, but not limited to Cy3 NHS ester; Cy 5 NHS ester; Cy5.5 NHSester; and Cy7 NHS ester.

It is within the ordinary skill in the art to select a suitable dye or dyes based on the desired spectral excitation and emission properties of the hydrogel particle.

Magnetic Hydrogel Particles

Figure 4A:
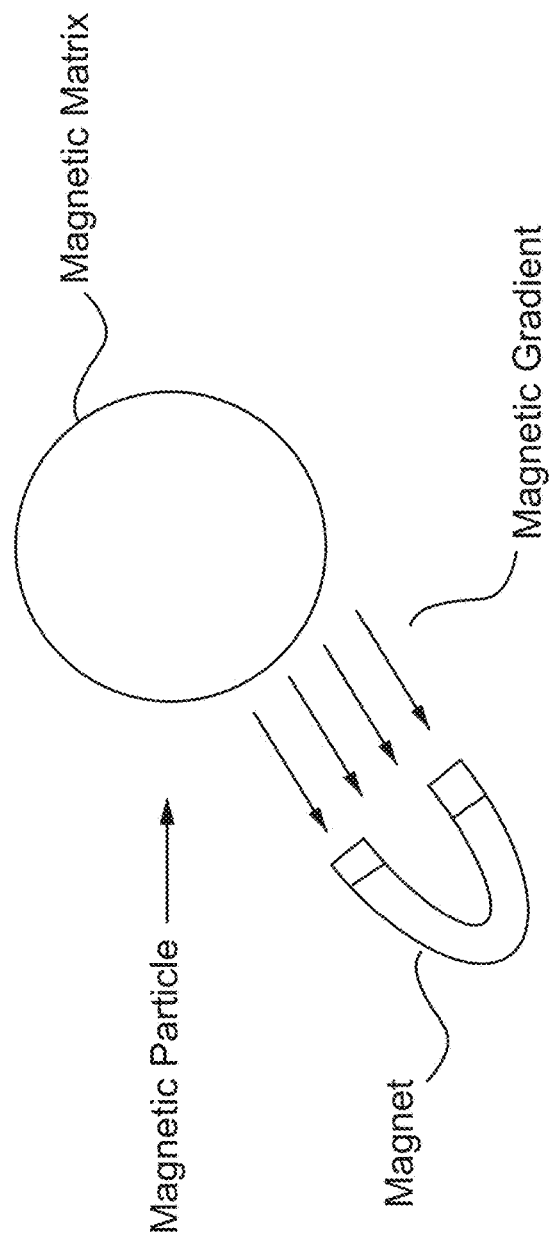
Figure 4B:
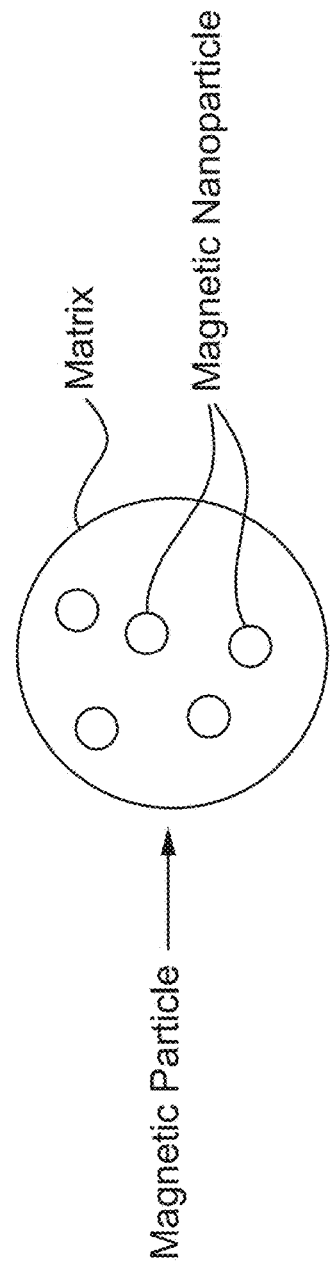
Figure 4C:
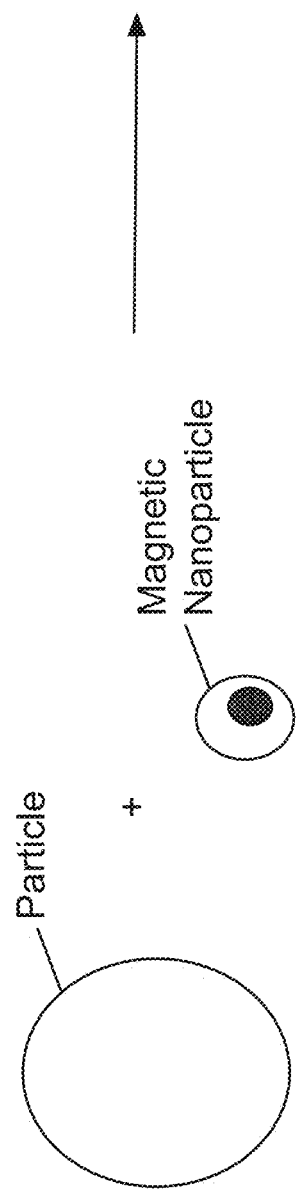

In some embodiments, a hydrogel particle can be magnetic, such that the hydrogel particle is capable of being attracted to or repelled by a magnetic field or a magnetic gradient introduced by a magnet. The hydrogel particle can be magnetic, diamagnetic, ferromagnetic, paramagnetic, or superparamagnetic. For example, to make the hydrogel particle magnetic, a magnetic bead, a magnetic particle, or magnetic nanoparticle (as shown in FIG. 4B and FIG. 4C), a magnetic fluid (e.g., a ferrofluid), combinations thereof, or the like can be encapsulated or embedded within the hydrogel particle. As yet another example, the hydrogel particle matrix can be composed of a magnetic material (e.g., magnetically-responsive hydrogels, such as those including iron oxide.

Figure 4F:
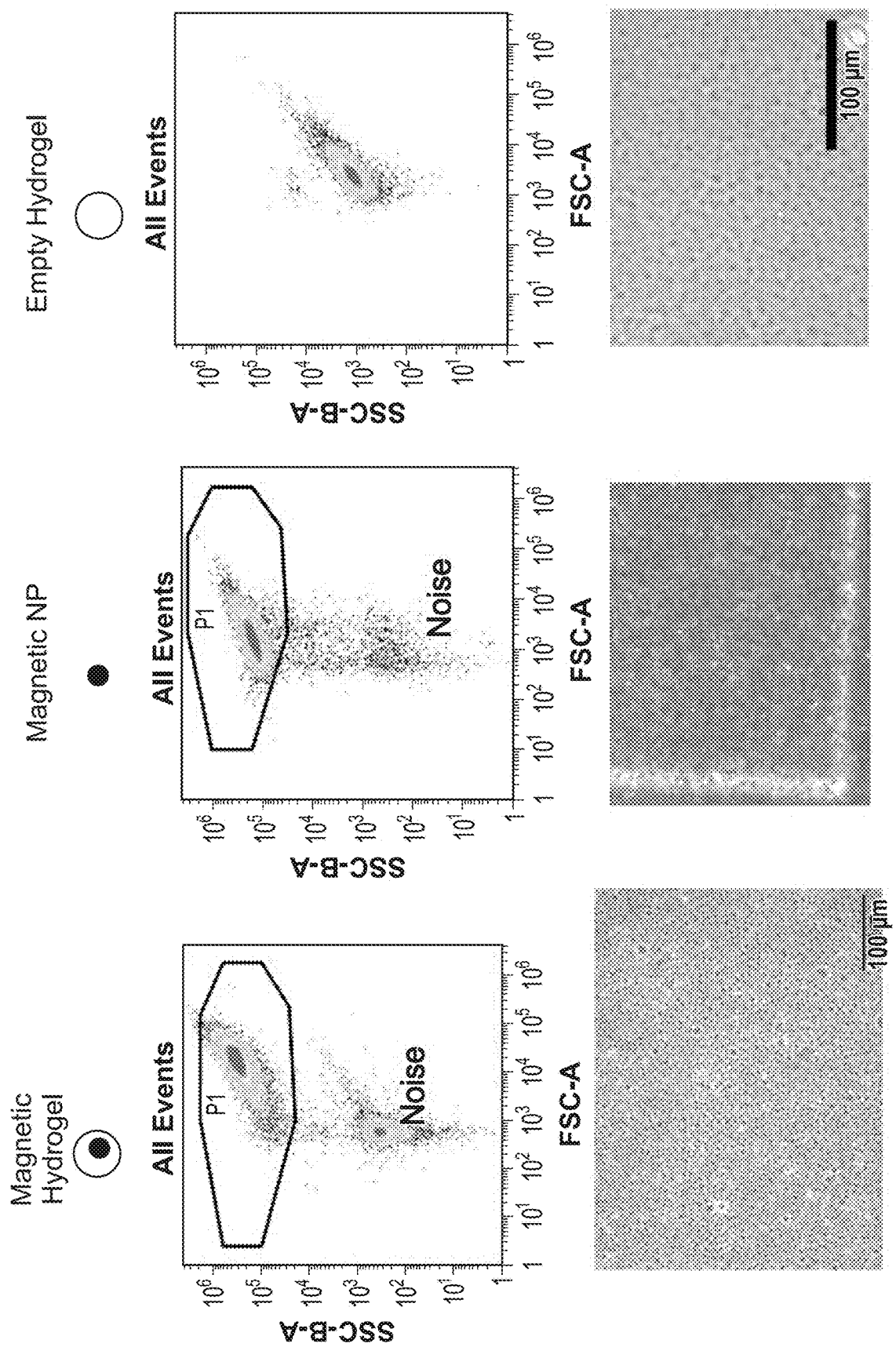
FIG. 4F provides graphical illustrations of performance of a magnetic hydrogel when compared with a magnetic nanoparticle and an empty hydrogel, according to embodiments of the present disclosure.

As shown in FIG. 4D through FIG. 4F, magnetic capture beads can be coated with antibodies targeting an extracellular biomarker on the target cell population. After incubation of a cell population with the capture beads (e.g., up to 1 minute, up to 2 minutes, up to 3 minutes, up to 4 minutes, up to 5 minutes, up to 10 minutes, up to 15 minutes, up to 30 minutes, up to 60 minutes, at least 60 minutes, or any appropriate time between, less than, or more than those times included), the magnetic capture beads specifically bind to the target cell population. Magnetic separation of capture bead-bound cells enriches for biomarker-positive cells from the host cell population. Beads can be dissolved or cleaved from the cells to recover the positive cells after magnetic capture.

Furthermore, as in FIG. 4F, inclusion of magnetic nanoparticles (e.g., superparamagnetic nanoparticles) in hydrogels or particles increases the side scatter of the hydrogel particles when measured on a flow cytometer.

The magnet can be, but is not limited to, a ring magnet, a bar magnet, a horseshoe magnet, an electromagnet, a switchable magnet, a spherical magnet, a polygon-shaped magnet, a polyhedral shape, a wand magnet, a kidney-shaped magnet, a trapezoidal magnet, a disk magnet, a cow magnet, or a block or brick magnet. When multiple magnets are used, the magnets may be different or the same in size, shape, and function (i.e., electromagnet versus permanent magnet).

In some embodiments, the magnetic hydrogel particles can be used for immunomagnetic separation of a target cell. In immunomagnetic separation, the magnetic hydrogel can be conjugated to the target cell via complementary ligands. The magnetic hydrogel particle can include a ligand, such as an antibody, directed to an antigen of the target cell. These complementary conjugates can bind to each other by covalent, ionic, dipole-dipole interactions, London dispersion forces, Van der Waal's forces, hydrogen bonding, or other chemical bonds. Direct or indirect conjugation can be used.

The target cell-magnetic hydrogel particle conjugate can then be attracted towards the magnet. The magnet creates a magnetic field or a magnetic gradient to attract the conjugate, as shown in FIG. 4A. The conjugate can be drawn out the sample of interest, towards a sidewall of a vessel, directed to a different bin, or the like.

In some embodiments, the magnetic hydrogel particles can be used to remove the magnetic hydrogel particles from a device or sample of interest before subsequent analysis. The magnetic hydrogel particles can be used as a control, such as for calibration or compensation. After the control step or process is completed, the magnetic hydrogel particles can be removed from the device being calibrated or the sample of interest for which compensation is being determined. Removing the magnetic hydrogel particles may be needed to avoid inclusion in incompatible steps or processes. For example, removal of the magnetic hydrogel particles can permit the sample to undergo subsequent processing or analysis (e.g., downstream analysis, sequencing, or the like) which can be incompatible with the magnetic hydrogel particles. As yet another example, removal of the magnetic hydrogel particles can permit the device to be used in subsequent processes in which the magnetic hydrogel particles are not compatible or in subsequent processes in which different magnetic hydrogel particles are to be used.

Hydrogel Particles Support Target Cell Growth

Feeder cells support the growth of target cells by releasing biomolecules such as growth factors, adhesion molecules, and/or extracellular matrix to the culture media, but can introduce issues such as viruses and unwanted antigens into the cell culture. Here, the present disclosure provides hydrogel particles that act as feeder cells and comprise one or more growth factors, adhesion molecules, and/or extracellular matrix to the culture media/target cells. In some aspects of the present disclosure the feeder hydrogel particles comprise one or more polypeptides or fragments thereof that support the growth of target cells. In some aspects of the present disclosure the feeder hydrogel particles comprise one or more polypeptides or fragments thereof that stimulate the proliferation and/or activation of the target cell.

In some embodiments, the biomolecules are attached to the surface of the hydrogel particle. In some embodiments, the biomolecules are in the matrix of the hydrogel particle itself. In some embodiments, the hydrogel is engineered to degrade to provide such biomolecule to the target cell. The rate of degradation can be modulated to provide slow degradation of the hydrogel particle and thus slow release of the biomolecule to the target cell. In some embodiments, the biomolecules are attached to both the surface of the hydrogel particle and in the matrix of the hydrogel particle. In some embodiments, the biomolecules on the surface and in the matrix of the hydrogel particle are the same. In some embodiments, the biomolecules on the surface and in the matrix of the hydrogel particle are different.

Antigen Presenting Hydrogel Particles

Though the present disclosure is described with reference to a T cell, the disclosure is not intended to be so limited in its scope of application. The present disclosure may be used for plasma cells, lymphocytes, immune cells, antigen presenting cells (e.g., dendritic cells, macrophages, B cells), naïve B cells, memory B cells, naïve T cells, memory T cells, chimeric antigen receptor T cell (CAR T cell), regulatory T cells, cytotoxic T cells, NK cells, or any other appropriate cell. Additionally, the method may be used for any number of cells or analytes, such as one, at least one, a plurality, etc.

Generally, T cell activation is triggered by a peptide antigen bound to a major histocompatibility complex (MHC) molecule on the surface of an antigen presenting cell (APC), a T cell receptor/CD3 complex (TCR/CD3). While this is the primary signal in T cell activation, other receptor-ligand interactions between APC and T cells are also required for full activation. For example, TCR stimulation in the absence of other molecular interactions can induce an anergic state such that these cells cannot respond to a complete activation signal upon restimulation. Thus, optimal functionality may be conferred through the use of a second signaling molecule, such as a membrane bound protein or APC secretion product. For these membrane-bound proteins, such second interactions are usually adhesive in nature and enhance the contact between the two cells. Other signaling molecules (eg, further activation signaling from APC to T cells) may also be relevant. For example, CD28 is a surface glycoprotein that is present in 80% of peripheral T cells in humans and is present in both quiescent and activated T cells. CD28 binds to B7-1 (CD80) or B7-2 (CD86) and is one of the most potent of the known costimulatory molecules. Combined with TCR engagement, CD28 ligation on T cells induces the production of interleukin-2 (IL-2). Secreted IL-2 is an important factor for ex vivo T cell expansion.

Here, the present disclosure provides hydrogel particles that act as APCs and comprise one or more biomolecules that stimulate the expansion and/or activation of a T cell. In some embodiments, the APC hydrogel comprises one or more of an activation biomolecule, a stimulatory biomolecule, a costimulatory biomolecule and/or a T cell homeostasis factor.

Furthermore, the present disclosure can detect, induce, or detect and induce activation events including, but not limited to, cell expansion, cell proliferation, cell differentiation, activation maintenance, cell maturation, cell receptor clustering, synapse formation (e.g., between a lymphocyte and a tumor cell), cytokine production, gene expression, protein expression, or any other appropriate occurrence by which the target cell is activated upon recognition of or stimulation by the proper antigen, antibody, immunoglobulin (e.g., CD3, CD19, CD20, CD28, CD80, CD86, CD69, CD154, CD137, IgM, IgG, IgE, IgA, IgD), toll-like receptors (TLR, such as, for example, TLR1-13), or the like.

In some embodiments, these activation events can be induced based on proximity of a hydrogel particle to a cell of interest. In one example, the hydrogel particle can be conjugated to the cell of interest, whether via direct or indirect conjugation. In another example, the hydrogel particle can be proximal to but not in contact with the cell of interest. The hydrogel particle and the cell of interest can be separated by less than 1 nm, less than 1 micron, less than 1 millimeter, or any appropriate separation distance by which the activation event can still occur.

Action may be distant from an area of introduction of the particle. in which a signal event or cascade event occurs remotely. The distance can be at least 1 millimeter, at least 1 centimeter, at least 1 meter, etc. For example, the particle may be introduced intramuscularly or intravenously and the action is in a lymph node or distant immune organ or other target organ. Alternatively the particle may be introduced on one side of a membrane and the action maybe on another side of a membrane (for e.g., via a semi-permeable membrane).

In some embodiments, the molecule that can stimulate T cell expansion and/or activation is a polypeptide or fragment thereof. In some embodiments, the polypeptide or fragment thereof that can stimulate T cell expansion and/or activation is a peptide antigen. In some embodiments, the molecule that can stimulate T cell expansion and/or activation is a component of a MHC molecule. In some embodiments, the molecule that can stimulate T cell expansion and/or activation is a component of a T cell receptor/CD3 complex. In some embodiments, the molecule that can stimulate T cell expansion and/or activation is an antibody that specifically binds a component of a T cell receptor/CD3 complex. In some embodiments, the hydrogel particle of the present disclosure comprises an antibody or fragment therefore that specifically binds to CD3.

In some embodiments, the hydrogel particle of the present disclosure comprises one or more T cell activation molecules and one or more T cell costimulatory molecules. In some embodiments, the hydrogel particle of the present disclosure comprises one or more antibodies or fragments thereof that specifically bind T cell activation molecules and one or more T cell costimulatory molecules. In some embodiments, the hydrogel particle of the present disclosure comprises a T cell activation molecule of CD3 and a T cell costimulatory molecule selected from CD28, ICOS, CD27, CD40, CD40L, CD137L, and CD137. In some embodiments, the hydrogel particle of the present disclosure comprises one or more antibodies or fragments thereof that specifically bind to CD3 and one or more antibodies or fragments thereof that specifically bind to CD28, ICOS, CD27, CD40, CD40L, CD137L, CD137, the like, or combinations thereof.

In some embodiments, the receptor molecule on the hydrogel/synthetic cell would be a MHC-tetramer (MHC class I or class II) and the CD3 CD28 molecules would be encapsulated within the hydrogel such that the primary recognition would be dictated by antigen-specificity by the MHC tetramer with the CD3, CD28 stimulation of such targeted cells occurring later with the consequence that only Ag-specific cells are co-stimulated allowing for lower magnitude of Cytokine Release Syndrome.

An embodiment of the present disclosure is to use APCs to eliminate a pathogenic subset of T-Cells, B-Cells, NK Cells or other immune cells. For example, to eliminate pathogenic T-cells in auto-immune disease. Take a synthetic cell, make it specific to a B-Cell which makes Abs against autoantigens as in Systemic Lupus Erythematosus (SLE). This results in elimination of B-Cells that produce Abs against various auto antigens.

In some embodiments, the T cell activation molecule may be an anti-CD3 antibody or an antigen-binding fragment thereof, an anti-macrophage scavenger receptor (MSR1) antibody or an antigen-binding fragment thereof, an anti-T cell receptor (TCR) antibody or an antigen-binding fragment thereof, an anti-CD2 antibody or an antibody thereof, antigen-binding fragments, anti-CD47 antibodies or antigen-binding fragments thereof, major histocompatibility complex (MHC) molecules loaded with MHC peptides or multimers thereof, and MHC-immunoglobulin (Ig) conjugates or multimers thereof, or combinations thereof.

In some embodiments, the hydrogel particle comprises one or more T cell costimulatory molecules including, but not limited to, CD28, 4.1BB (CD137), OX40 (CD134), CD27 (TNFRSF7), GITR (CD357), CD30 (TNFRSF8), HVEM (CD270), LTβR (TNFRSF3), DR3 (TNFRSF25)), ICOS (CD278), CD226 (DNAM1), CRTAM (CD355), TIM1 (HAVCR1, KIM1), CD2 (LFA2, OX34), SLAM (CD150, SLAMF1), 2B4 (CD244, SLAMF4), Ly108 (NTBA, CD352), SLAMF6), CD84 (SLAMF5), Ly9 (CD229, SLAMF3) and/or CRACC (CD319, BLAME). In some embodiments, the hydrogel particles comprises one or more antibodies or fragments thereof that specifically bind to CD28, 4.1BB (CD137), OX40 (CD134), CD27 (TNFRSF7), GITR (CD357), CD30 (TNFRSF8), HVEM (CD270), LTβR (TNFRSF3), DR3 (TNFRSF25)), ICOS (CD278), PD1 (CD279) CD226 (DNAM1), CRTAM (CD355), TIM1 (HAVCR1, KIM1), CD2 (LFA2, OX34), SLAM (CD150, SLAMF1), 2B4 (CD244, SLAMF4), Ly108 (NTBA, CD352), SLAMF6), CD84 (SLAMF5), Ly9 (CD229, SLAMF3) and/or CRACC (CD319, BLAME). In some embodiments, the hydrogel particle of the present disclosure comprises an anti-CD28 antibody or fragment thereof.

In some embodiments, the hydrogel particle of the present disclosure comprises one or more polypeptides that promote expansion of a particular T cell subtype while simultaneously inhibiting the development of the other subset. In some embodiments, the polypeptide that promotes expansion of a particular T cell subtype is a cytokine. In some embodiments, the cytokine is an interleukin, interferon, lymphotoxin, a member of the TNF superfamily, or an antibody or fragment thereof that binds to one of the foregoing. In some embodiments, the cytokine is selected from a list including, but not limited to, IL-1, IL-2, IL-4, IL-5, IL-7, IL-10, IL-12, IL-15, IL-17, IL-21, interferon γ, IFN alpha, IFN beta, lymphotoxin α, TNFα, TNFβ or a combination thereof.

In some embodiments, the hydrogel particle of the present disclosure comprises one or more T cell homeostasis factors. In some embodiments, the T cell homeostasis factor is selected from a list including, but not limited to, transforming growth factor 13 (TGF-(3), or agonists thereof, mimetics thereof, variants thereof, functional fragments thereof, or a combination thereof. In some embodiments, the T cell homeostasis factor is IL-2, an agonist, mimetic, variant, or functional fragment or a combination thereof.

In some embodiments, the hydrogel particle comprises a CD3 and a CD28 biomolecule or fragment thereof. In some embodiments, the hydrogel particle comprises an anti-CD3 and an anti-CD28 antibody or fragment thereof.

In some embodiments, the biomolecules are attached to the surface of the hydrogel particle (e.g., an APC hydrogel or a feeder hydrogel). In some embodiments, the biomolecules are in the matrix of the hydrogel particle itself (e.g., encapsulated or embedded within the hydrogel particle). In some embodiments, the biomolecules are attached to both the surface of the hydrogel particle and in the matrix of the hydrogel particle. In some embodiments, the biomolecules on the surface and in the matrix of the hydrogel particle are the same. In some embodiments, the biomolecules on the surface and in the matrix of the hydrogel particle are different.

In some embodiments, the T cell stimulated and/or expanded and or depleted/removed by the hydrogel particle of the present disclosure is selected from the nonlimiting group consisting of natural killer (NK) cells, CD3+ T cells, CD4+ T cells, CD8+ T cells, and regulatory T cells (Treg), or a combination thereof. In some embodiments, the T cell is a helper T cell. In some embodiments, the T cell is a cytotoxic T cell. In some embodiments, the T cell is a Th1 or a Th2 cell. In some embodiments, the T cell is a recombinant T cell. In some embodiments, the recombinant T cell is a CAR T cell.

In some embodiments, the T cell is freshly collected from a subject. In some embodiments, the T cell is a cultured cell line. In some embodiments, the T cell is an established cell line. In some embodiments, the T cell is cultured from a preserved or frozen sample.

In some embodiments, the hydrogel particles of the present disclosure induce the expansion, proliferation, and/or activation of any appropriate T cell. In some embodiments, the T cell does not expand, proliferate, and/or activate in culture without the APC hydrogel particles. In some embodiments, the T cell does not expand, proliferate, and/or activate well in culture without the APC hydrogel particles.

In some embodiments, the T cells, or subsets thereof are eliminated as a consequence of incubating with the APC hydrogel particles.

In some embodiments, the T cells are derived from any appropriate source within an animal. The animals from which the T cells are harvested may be vertebrate or invertebrate, mammalian or non-mammalian, human or non-human Examples of animal sources include, but are not limited to, primates, rodents, canines, felines, equines, bovines and porcines.

In some embodiments, a target cell is an immune cell. Non-limiting examples of immune cells include B lymphocytes, also called B cells, T lymphocytes, also called T cells, natural killer (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor infiltrating (TIL) cells, gene modified immune cells including hybridomas, drug modified immune cells, and derivatives, precursors or progenitors of any of the cell types listed herein.

In some embodiments, a target cell encompasses all cells of a particular class of cell with shared properties. For example, a target cell can be a lymphocyte, including NK cells, T cells, and B cells. A target cell can be an activated lymphocyte.

In some embodiments, a target cell is a primary cell, cultured cell, established cell, normal cell, transformed cell, infected cell, stably transfected cell, transiently transfected cell, proliferating cell, or terminally differentiated cells.

In one embodiment, a target cell is a primary neuronal cell. A variety of neurons can be target cells. As non-limiting examples, a target cell can be a primary neuron; established neuron; transformed neuron; stably transfected neuron; or motor or sensory neuron.

In other embodiments, a target cell is selected from the group consisting of: primary lymphocytes, monocytes, and granulocytes.

A target cell can be virtually any type of cell, including prokaryotic and eukaryotic cells.

Suitable prokaryotic target cells include, but are not limited to, bacteria such as *E. coli*, various *Bacillus* species, and the extremophile bacteria such as thermophiles.

Suitable eukaryotic target cells include, but are not limited to, fungi such as yeast and filamentous fungi, including species of *Saccharomyces, Aspergillus, Trichoderma,* and *Neurospora*; plant cells including those of corn, sorghum, tobacco, canola, soybean, cotton, tomato, potato, alfalfa, sunflower, etc.; and animal cells, including fish, birds and mammals. Suitable fish cells include, but are not limited to, those from species of salmon, trout, tilapia, tuna, carp, flounder, halibut, swordfish, cod and zebrafish. Suitable bird cells include, but are not limited to, those of chickens, ducks, quail, pheasants and turkeys, and other jungle fowl or game birds. Suitable mammalian cells include, but are not limited to, cells from horses, cows, buffalo, deer, sheep, rabbits, rodents such as mice, rats, hamsters and guinea pigs, goats, pigs, primates, marine mammals including dolphins and whales, as well as cell lines, such as human cell lines of any tissue or stem cell type, and stem cells, including pluripotent and non-pluripotent, and non-human zygotes.

Suitable target cells also include those cell types implicated in a wide variety of disease conditions, even while in a non-diseased state. Accordingly, suitable eukaryotic cell types include, but are not limited to, tumor cells of all types (e.g., melanoma, myeloid leukemia, carcinomas of the lung, breast, ovaries, colon, kidney, prostate, pancreas and testes), cardiomyocytes, dendritic cells, endothelial cells, epithelial cells, lymphocytes (T-cell and B cell), mast cells, eosinophils, vascular intimal cells, macrophages, natural killer cells, erythrocytes, hepatocytes, leukocytes including mononuclear leukocytes, stem cells such as hematopoietic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. In certain embodiments, the cells are primary disease state cells, such as primary tumor cells. Suitable cells also include known research cells, including, but not limited to, Jurkat T cells, NIH3T3 cells, CHO, COS, etc. See the ATCC cell line catalog, hereby expressly incorporated by reference.

In some embodiments, a target cell is a tumor microvesicle or tumor macrovesicle. Tumor microvesicles, also known as tumor-secreted microvesicles or tumor-secreted exosomes, can be found in circulating blood and may have immune-suppressive activities. Tumor microvesicles typically range in size from 30-200 nm in diameter. Larger tumor micro vesicles may be referred to as tumor macro vesicles, and can range in size from 3-10 µm in diameter.

In some aspects the hydrogel particles of the present disclosure support the growth of any appropriate target cell. In some embodiments, the target cell does not proliferate in culture without the feeder hydrogel particles. In some embodiments, the target cell does not proliferate well in culture without the feeder hydrogel particles.

In some embodiments, the target cell is a stem cell. In some embodiments, the stem cell is, without limitation, an embryonic stem cell, a ICM/epiblast cell, a primitive ectoderm cell, a primordial germ cell, a cancer cell, or a teratocarcinoma cell.

In some embodiments, the stem cell is a pluripotent stem cell, a totipotent stem cell, a multipotent stem cell, an oligopotent, or a unipotent stem cell. In some embodiments, the pluripotent stem cell is an embryonic stem cell. In some embodiments, the stem cell is an undifferentiated pluripotent stem cell. In some embodiments, the totipotent stem cell is, without limitation, an embryonic stem cell, a neural stem cell, a bone marrow stem cell, a hematopoietic stem cell, a cardiomyocytes, a neuron, an astrocyte, a muscle cell, or a connective tissue cell. In some embodiments, the multipotent stem cell is, without limitation, a myeloid progenitor cell, or a lymphoid progenitor cell. In some embodiments, the stem cell is an induced pluripotent stem cell (iSPC). In some embodiments, the stem cell is an adult stem cell. In some embodiments, the stem cell is an undifferentiated pluripotent stem cell. In some embodiments, the stem cell is a mammalian stem cell. In some embodiments, the stem cell is a primate stem cell. In some embodiments, the stem cell is a human stem cell.

In some embodiments, the stem cells are derived from any source within an animal. For example, stem cells may be harvested from embryos, or any primordial germ layer therein, from placental or chorion tissue, or from more mature tissue such as adult stem cells including, but not limited to adipose, bone marrow, nervous tissue, mammary tissue, liver tissue, pancreas, epithelial, respiratory, gonadal and muscle tissue. In some embodiments, the stem cells are placental- or chorionic-derived stem cells.

In some embodiments, the present disclosure contemplates using differentiable cells from any animal capable of generating differentiable cells, e.g., pancreatic type cells such as beta cells. The animals from which the differentiable cells are harvested may be vertebrate or invertebrate, mammalian or non-mammalian, human or non-human. Examples of animal sources include, but are not limited to, primates, rodents, canines, felines, equines, bovines and porcines.

In some embodiments, the target cell is a blood cell. In some embodiments, the target cell is a peripheral blood mononuclear cell (PMBC). In some embodiments, the peripheral blood mononuclear cell is a lymphocyte, a monocyte, or a dendritic cell. In some embodiments, the lymphocyte is a T-cell, B-cell, or NK cell. In some embodiments, the target cell is a natural killer (NK) cell.

In certain embodiments of the present disclosure, the cell culture is enriched. The term "enriched" refers to a cell culture that contains at least 10%, 15%, 20%, 25%, 30%, 35%, 40%, 45%, 50%, 55%, 60%, 65%, 70%, 75%, 80%, 85%, 90%, 95%, or 100% of the desired cell lineage.

As used herein, the term "substantially undifferentiated" cell culture refers to a population of stem cells comprising at least about 50%, preferably at least about 60%, 70%, or 80%, and even more preferably, at least about 90%, undifferentiated, stem cells. Fluorescence-activated cell sorting using labeled antibodies or reporter genes/proteins (e.g., enhanced green fluorescent protein [EGFP]) to one or more markers indicative of a desired undifferentiated state can be used to determine how many cells of a given stem cell population are undifferentiated. For purposes of making this assessment, one or more cell surface markers correlated with an undifferentiated state (e.g., SSEA-4, Tra-1-60, and Tra-1-81), as well as the typical pluripotent stem cell transcription factor marker, Oct-4, can be detected. Telomerase reverse transcriptase (TERT) activity and alkaline phosphatase can also be assayed. In the context of primate stem cells, positive and/or negative selection can be used to detect, for example, by immuno-staining or employing a reporter gene (e.g., EGFP), the expression (or lack thereof) of certain markers (e.g., Oct-4, SSEA-4, Tra-1-60, Tra-1-81, SSEA-1, S SEA-3, nestin, telomerase, Myc, p300, and Tip60 histone acetyltransferases, and alkaline phosphatase activity) or the presence of certain post-translational modifications (e.g., acetylated histones), thereby facilitating assessment of the state of self-renewal or differentiation of the cells. Also, undifferentiated cells described herein have typical stem cell morphology which is well described in the art.

In some aspects of the present disclosure, the feeder hydrogel particle comprises one or more molecules that support cell growth and/or stimulate target cell proliferation or activation. These molecules include, but are not limited to, cytokines, growth factors, cytokine receptors, extracellular matrix, transcription factors, secreted polypeptides and other molecules, and growth factor receptors, or fragments thereof. In some embodiments, the feeder hydrogel particle comprises a fibroblast growth factor (bFGF), an acidic fibroblast growth factor (aFGF), an epidermal growth factor (EGF), insulin-like growth factor-1 (IGF-I), insulin-like growth factor-II (IGF-II), a platelet-derived growth factor-AB (PDGF), a vascular endothelial cell growth factor (VEGF), activin-A, a bone morphogenic protein (BMP), a chemokine, a morphogen, a neutralizing antibody, a heregulin, an interferon, a macrophage-derived cytokine, an interleukin, an interleukin receptor, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, 11-23, IL-24, IL-25, IL-26, IL-28, IL-29, IL-30, IL-31, IL-32, IL-33, IL-34, IL-35, IL-36, IL-37, IL-38, tumor necrosis factor, TNFα, TNFβ, TNFR1, TNFR2, IFAR1, IFAR2, TGFR1, TGFR2, FGF, granulocyte macrophage colony-stimulating factor, chemokines (e.g. CCL1, CCL2, CCL3, CCL, CCL5, and CXCL8), CD27 ligand (CD27L), CD40L, CD137L, TNF-related apoptosis-inducing ligand (TRAIL), TNF-related activation-induced cytokine (TRANCE), TNF-related weak inducer of apoptosis (TWEAK), B cell activating factor (BAFF), LIGHT (homologous to lymphotoxin, exhibits inducible expression and competes with herpes simplex virus glycoprotein D for binding to herpesvirus entry mediator, a receptor expressed on T lymphocytes), TNF-like cytokine 1A (TL1A), glucocorticoid-induced TNF receptor-related protein ligand (GITRL), transforming growth factor α (TGF-α), TGF-β, vascular endothelial growth factor (VEGF), nerve growth factor (NGF), macrophage colony-stimulating factor (M-CSF), granulocyte-macrophage colony-stimulating factor (GM-CSF), IFN-α, IFN-β, and IFN-γ.

In some embodiments, the biomolecules on the surface and in the matrix of the hydrogel particle are different and the components of the matrix dissolve at different rates.

In some embodiments, the hydrogel particles are engineered to degrade to provide such biomolecules to a cell in culture. Degradation can include, without limitation, dissolution (i.e., dissolving) or lysis. The hydrogel can be engineered to have multiple layers, as shown in FIG. 1, with different rates of degradation for at least two of the layers. The hydrogel, whether in its entirety or various layers thereof, can be degraded chemically (e.g., reagents, detergents, bursting, or the like), mechanically (e.g., vibration, acoustic, freeze-thaw, bursting, or the like), or both chemically and mechanically.

The rate of degradation of the entire hydrogel particles, individual layers of the hydrogel particles, or groups or subpopulations of a hydrogel population can be fast (i.e., less than 24 hours) or slow (i.e., 24 hours or more). For example, a first layer of a hydrogel particle can degrade in less than 24 hours and a second layer of the same hydrogel particle can degrade in 48 hours. As yet another example, a first subpopulation of hydrogel particles can degrade in less than 1 hour, a second subpopulation of hydrogel particles can degrade in 24 hours, and a third subpopulation of hydrogel particles can degrade in one week. The first, second, and third subpopulations form a population of hydrogel particles.

In some embodiments, a population of hydrogel particles can include groups or subpopulations of hydrogel particles having different rates of degradation.

In some embodiments, the hydrogel particle can be engineered to have pore sizes which correlate to various rates of degradation. The pore sizes can range from 0.1 nm to 1 μm. For example, a first hydrogel particle can have a first pore size, such that the first hydrogel particle has a first rate of degradation; and, a second hydrogel can have a second pore size, such that the second hydrogel particle has a second rate of degradation with the first and second rates of degradation not being equal (e.g., first rate is faster than the second rate; or, the first rate is slower than the second rate).

In some embodiments, the hydrogel particle can be engineered to have a rate of degradation based on a plurality of factors, including, without limitation, pore size, chemical composition (i.e., chemical bonds, monomers, co-monomer), layer composition, the like, and combinations thereof.

In some embodiments, the hydrogel particle contains growth factor, cytokines or hormone precursors that must be processed by a protease to release the active growth factor. In some embodiments the corresponding proteases capable of producing the active growth factor may be added to the growth media, naturally secreted by the target cells or included in the composition of the hydrogel particles.

In some embodiments, the hydrogel particle contains disulfide cross links enabling the hydrogel particle to dissolve upon the addition of a reducing agent. In some embodiments the hydrogel particle can be dissolved by the addition of a protease. In some embodiments the growth factors are crosslinked to each other or to the hydrogel matrix via disulfide crosslinks that may be broken by the addition of a reducing agent, releasing active growth factors. Appropriate reducing agents may include but are not limited to dithiothreitol, Tris(2-carboxyethyl)phosphine hydrochloride and 2-mercaptoethanol. In some embodiments, the feeder hydrogel particle comprises only one type of molecule that supports cell growth and/or stimulates target cell proliferation or activation. In some embodiments, the feeder hydrogel particle comprises only one class of molecule that supports target cell growth and/or stimulates target cell proliferation or activation. In some embodiments, the feeder hydrogel particle comprises multiple types and/or classes of molecules that support cell growth and/or stimulate target cell proliferation or activation.

In some embodiments, the feeder hydrogel particle comprises an interleukin and a cell surface molecule. In some embodiments, the feeder hydrogel particle comprises at least two interleukins and a cell surface molecule. In some embodiments, the feeder hydrogel particle comprises IL-2, IL-15, IL-21, CD137L, and CD137 (TNPRSF9; 4-1BB). In some embodiments, the feeder hydrogel particle comprises IL-15, IL-21, CD137L, and CD137 and activates NK cells.

In some embodiments, the feeder hydrogel particle comprises one or more components of the extracellular matrix. In some embodiments, the feeder hydrogel particle provides physical support for the target cells.

In some embodiments, the feeder hydrogel particle comprises between about 1 and about 100,000,000 copies of one or more molecules that support cell growth and/or stimulate target cell proliferation or activation. In some embodiments, the feeder hydrogel particle is approximately the same size as the target cell, and comprises between about 500 and 100,000,000 copies of one or more molecules that support cell growth and/or stimulate target cell proliferation or activation. In some embodiments, the feeder hydrogel particle is approximately about 5 μm to about 200 μm, and comprises between about 500 and 100,000,000 copies of one or more molecules that support cell growth and/or stimulate target cell proliferation or activation. In some embodiments, the hydrogel particle has a diameter of at least 5 nm, In some embodiments, the feeder hydrogel particle comprises at least the same number of the one or more molecules that support cell growth and/or stimulate target cell proliferation or activation as binding sites of the target cell. In some embodiments, the feeder hydrogel particle comprises more of the one or more molecules that support cell growth and/or stimulate target cell proliferation or activation as binding sites of the target cell. In some embodiments, the feeder hydrogel particle comprises at least 1, at least 10, at least 100, at least 1,000, at least 10,000, at least 100,000, at least 1,000,000, at least 10,000,000, or at least 100,000,000 copies of one or more molecules that support cell growth and/or stimulate target cell proliferation or activation.

In one embodiment, a plurality of hydrogel particles is used to determine the dynamic range and/or sensitivity of detection of a particular cell surface marker or combination thereof on a population of target cells. For example, the population of hydrogel particles can be tuned to have the SSC and/or FSC profile of the target cell, and subpopulations of the hydrogel particle are derivatized with a specific number of copies of a cell surface marker, e.g., a cell surface receptor, or a domain thereof, for example, an epitope binding region thereof. For example, individual subpopulations of hydrogel particles can each be derivatized to have a unique number of copies, e.g., one subpopulation will contain 100 copies of a cell surface marker, a second subpopulation will contain 1,000 copies of the same cell surface marker, a third subpopulation will contain 10,000 copies of the same cell surface marker, etc. The populations of hydrogel particles are fluorescently stained for the respective cell surface marker and fluorescence is detected for hydrogel particles in each subpopulation. In this regard, the subpopulations of hydrogel particles can be used to generate a standard curve of fluorescence emission for target cells with the respective cell marker. The cell surface marker can be any of the cell surface markers provided thereof, or binding regions thereof, or a cell surface marker known to one of ordinary skill in the art.

In some aspects, the present disclosure provides methods of culturing a target cell with one or more feeder hydrogel particles as described herein. In some aspects, the culturing media is useful in culturing the target cells. In some embodiments, the media is substantially isotonic as compared to the cells being cultured. In some embodiments where undifferentiated stem cells are cultured, the particular medium comprises a base medium and an amount of various factors necessary to support substantially undifferentiated growth of embryonic stem cells. In some embodiments, the base medium comprises salts, essential amino acids, a carbon source that can be metabolized by the target cells, and human serum. In some embodiments, for instance when the target cell is a T cell, the base medium comprises cytokines such as IL-2, IL-7, and IL-15. All these ingredients are supplied in an amount that will support respective target cells.

Figures 5A, 5B:
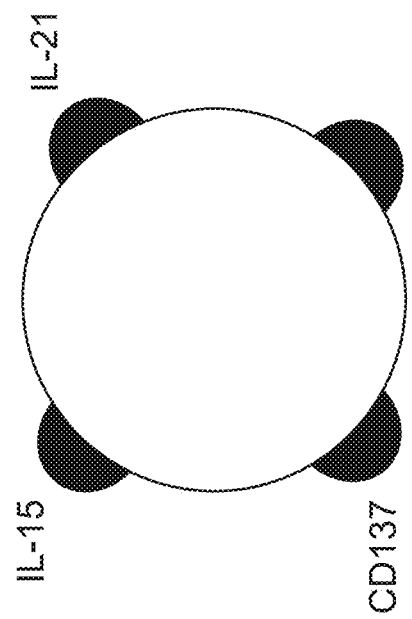
FIG. 5A and FIG. 5B relate to hydrogel particles as feeder cells, according to embodiments of the present disclosure.

In some embodiments, the disclosure provides a cell culture composition comprising a target cell, a defined culture media comprising human serum (hS), and a feeder hydrogel particle as described herein, and wherein the composition is essentially free of feeder cells. In some embodiments, the disclosure provides a cell culture composition comprising a natural killer cell, a defined culture media comprising human serum (hS), and a feeder hydrogel particle as described herein, and wherein the composition is essentially free of feeder cells. In some embodiments, the disclosure provides a cell culture composition comprising an natural killer cell, a defined culture media comprising human serum (hS), and a feeder hydrogel particle as described herein comprising one or more of an interleukin and/or a member of the tumor necrosis factor superfamily, and wherein the composition is essentially free of feeder cells. In some embodiments, the disclosure provides a cell culture composition comprising a natural killer cell, a defined culture media comprising human serum (hS), and a feeder hydrogel particle as described herein comprising one or more of IL-15, IL-21, CD137L, and/or CD137 and wherein the composition is essentially free of feeder cells. In some embodiments, the disclosure provides a cell culture composition comprising a natural killer cell, a defined culture media comprising human serum (hS), and different feeder hydrogel particles as described herein comprising one or more of IL-15, IL-21, CD137L and/or CD137 and wherein the composition is essentially free of feeder cells. In some embodiments, the disclosure provides, as partially shown in FIG. 5A and as partially described in FIG. 5B, a feeder hydrogel particle comprising IL-15, IL-21, CD137L, and CD137.

In some embodiments, the disclosure provides a cell culture composition comprising a T cell, a defined culture media comprising human serum (hS), and an APC hydrogel particle as described herein, and wherein the composition is essentially free of feeder cells. In some embodiments, the disclosure provides a cell culture composition comprising a B cell, a defined culture media comprising human serum (hS), and a CD19-expressing APC hydrogel particle as described herein, and wherein the composition is essentially free of feeder cells. In some embodiments, the disclosure provides a cell culture composition comprising a T cell, a defined culture media comprising human serum (hS), and an APC hydrogel particle as described herein comprising one or more antibodies or fragments thereof that specifically bind CD3 and one or more antibodies or fragments thereof that specifically bind CD28, and wherein the composition is essentially free of feeder cells.

In some embodiments, the disclosure provides a cell culture composition comprising a T cell, a defined culture media comprising human serum (hS), and an APC hydrogel particle, as shown in FIG. 6A and FIG. 6B, comprising one or more antibodies or fragments thereof that specifically bind CD3 and one or more antibodies or fragments thereof that specifically bind CD28, and wherein the composition is essentially free of feeder cells.

Figure 7C:
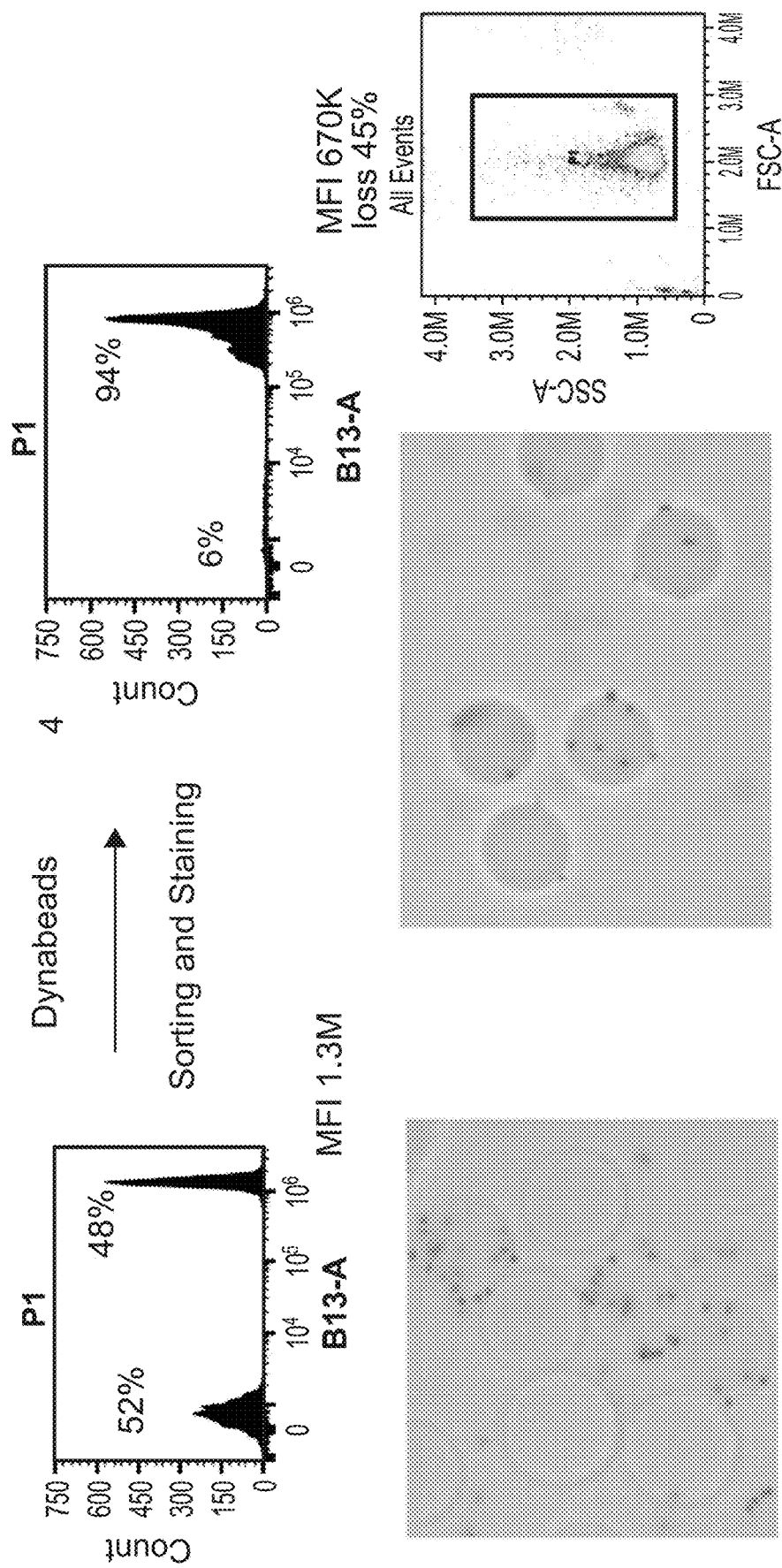
FIG. 7C shows cell capture with anti-CD4 Dynabeads. A 1:1 CD4 positive to negative mixture was used. Selection with Dynabeads was able to select CD4+ cells from mixture at 94% purity and 55% yield.
Figure 7D:
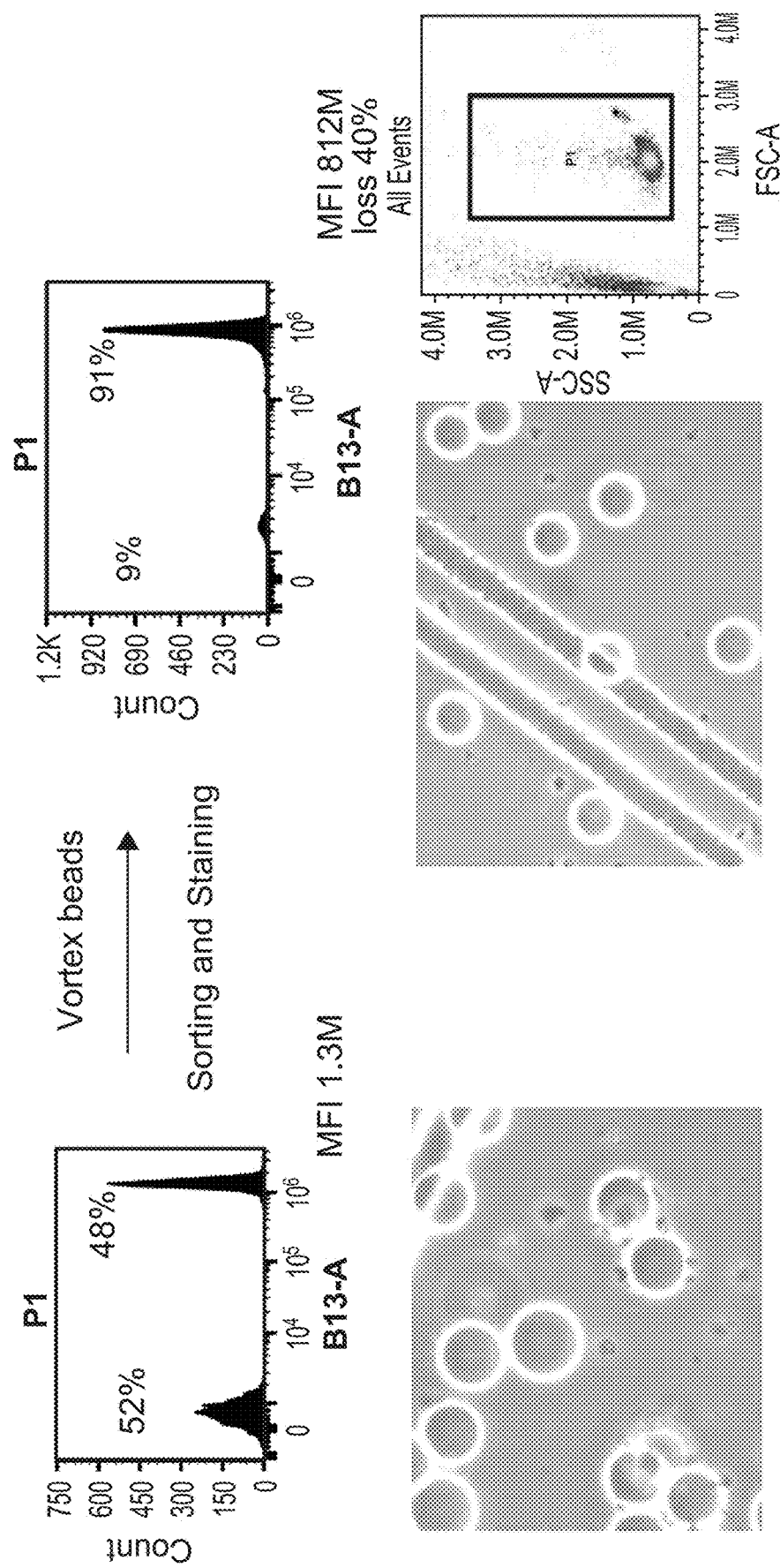
FIG. 7D shows CD4+ Cell capture with anti-CD4 capture beads. Similar performance is shown to Dynabeads with 91% purity and 60% yield of CD4+ cells after purification from a 1:1 mixture of positive and negative cells.

In some embodiments, the disclosure provides a cell culture composition comprising a lymphocyte, a defined culture media comprising hS, and an APC hydrogel particle, as shown in FIG. 7A, comprising one or more antibodies or fragments thereof that specifically bind CD4. As shown in FIG. 7A, staining anti-CD4-conjugated magnetic nanoparticle containing hydrogels with a fluorescently labeled secondary antibody shows a mean fluorescence intensity (MFI) of 190k indicating that the hydrogels contain a significant amount of bound anti-CD4. FIG. 7B shows that capture beads can bind specifically with hydrogel lymphocyte mimics. Top panels of FIG. 7B show positive control interactions between streptavidin and biotin hydrogels. Bottom panels of FIG. 7B show Anti-CD4 beads with CD4+ hydrogels. Further, as shown in FIG. 7C, cell capture with anti-CD4 Dynabeads at 1:1 CD4 positive to negative mixture is shown. Selection with Dynabeads selected CD4+ cells from a mixture at 94% purity and 55% yield. As shown in FIG. 7D, CD4+ cell capture with anti-CD4 capture beads showed similar performance to Dynabeads with 91% purity and 60% yield of CD4+ cells after purification from a 1:1 mixture of positive and negative cells.

Figure 8B:
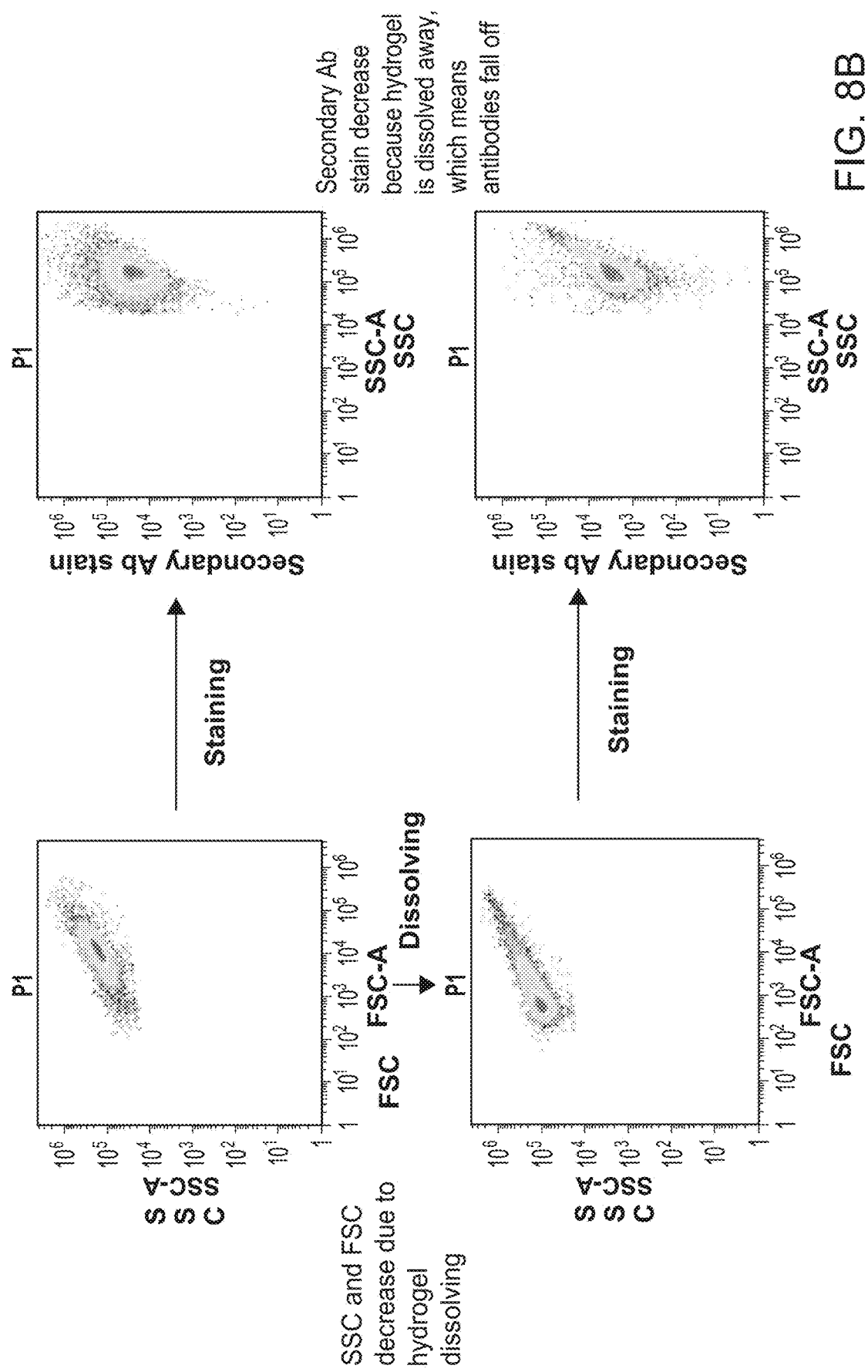
FIG. 8B shows that magnetic capture particles can be cleaved from positively selected cells or dissolved to be removed from positively selected cells. Doing so decreases the side scatter and the forward scatter. Secondary antibody staining also decreases because magnetic capture particles that are dissolved away cause antibodies to fall off.

In embodiments, as shown in FIG. 8A and FIG. 8B, magnetic capture particles can be cleaved from positively selected cells or dissolved to be removed from positively selected cells. Doing so decreases the side scatter and the forward scatter. Secondary antibody staining also decreases because magnetic capture particles that are dissolved away cause antibodies to fall off.

The present disclosure includes a defined media further comprising various amounts of human serum, for example, from about 0.5% to about 40%, from about 0.5% to about 30%, from about 0.5% to about 20%, from about 0.5% to about 10%, from about 0.5% to about 5%, from about 0.5% to about 3%, from about 0.5% to about 2%, and from about 0.5% to about 1%. However, typical defined media stem cell cultures use the term "essentially serum-free" which refers to exogenously added serum or serum components. Serum added in such media is typically in greater amounts than that described herein. Of course, if the cells being cultured produce some or all of the components of serum, or if the cells to be cultured are derived from a seed culture grown in a medium that contained serum, the incidental co-isolation and subsequent introduction into another culture of some small amount of serum (e.g., less than about 1%) should not be deemed as an intentional introduction of serum.

In some embodiments, the cells and the hydrogels are cultured in media comprising synthetic media supplements and are serum-free.

In some embodiments, the feeder hydrogel particles form a single monolayer in the cell culture. In some embodiments, the feeder hydrogel particles form a multi-layer support in the cell culture.

In some embodiments, the cell culture comprises a single type of feeder hydrogel particle. In some embodiments, the cell culture comprises a combination of different types of feeder hydrogel particles.

In some embodiments, the cell culture comprises between about $1\times10^5$ and about $1\times10^8$ feeder hydrogel particles per mL of cell culture. In some embodiments, the cell culture comprises about $1\times10^5$, about $1\times10^6$, about $1\times10^7$, or about $1\times10^8$ feeder hydrogel particles per mL of cell culture. In some embodiments, the cell culture comprises a similar concentration of feeder hydrogel particles as feeder cells used in traditional cell culturing methods.

In some embodiments, the feeder hydrogel particles of the present disclosure are applied to the cell culture at a dilution of about 1:1 to about 1:1000. In some embodiments, the feeder hydrogel particles are applied to the cell culture at a dilution of about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, about 1:100, about 1:200, about 1:300, about 1:400, about 1:500, about 1:600, about 1:700, about 1:800, about 1:900, or about 1:1000.

In some embodiments, culturing the target cell with a feeder hydrogel particle of the present disclosure increases target cell proliferation by about 1% to about 10000% compared to culturing of the target cell without the feeder hydrogel particle. In some embodiments, target cell proliferation is increased by about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, about 1000%, about 2000%, about 3000%, about 4000%, about 5000%, about 6000%, about 7000%, about 8000%, about 9000%, or about 10000% compared to culturing of the target cell without the feeder hydrogel particle. In some embodiments, cell proliferation can be at least $100,000\times$ the initial cell population.

In some embodiments, culturing the target cell with a feeder hydrogel particle of the present disclosure increases target cell activation by about 1% to about 10000% compared to culturing of the target cell without the feeder hydrogel particle. In some embodiments, target cell proliferation is increased by about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, about 1000%, about 2000%, about 3000%, about 4000%, about 5000%, about 6000%, about 7000%, about 8000%, about 9000%, or about 10000% compared to culturing of the target cell without the feeder hydrogel particle. In some embodiments, cell activation can be at least $100,000\times$ the initial cell population.

In some embodiments, the feeder cells can support culturing or proliferation based on proximity of a hydrogel particle to a cell of interest. In one example, the hydrogel particle can be conjugated to the cell of interest, whether via direct or indirect conjugation. In another example, the hydrogel particle can be proximal to but not in contact with the cell of interest. The hydrogel particle and the cell of interest can be separated by less than 1 nm, less than 1 micron, less than 1 millimeter, or any appropriate separation distance by which the activation event can still occur.

Culturing or proliferation may be distant from an area in which the cell of interest is located (i.e., culturing or proliferation can occur remotely). The distance can be at least 1 millimeter, at least 1 centimeter, at least 1 meter, etc. For example, the particle may be introduced intramuscularly or intravenously and the action is in a lymph node or distant immune organ or other target organ. Alternatively the particle may be introduced on one side of a membrane and the action maybe on another side of a membrane (for e.g., via a semi-permeable membrane).

In some embodiments, the APC hydrogel particles form a single monolayer in the cell culture. In some embodiments, the APC hydrogel particles form a multi-layer support in the cell culture.

In some embodiments, the cell culture comprises a single type of APC hydrogel particle. In some embodiments, the cell culture comprises a combination of different types of APC hydrogel particles.

In some embodiments, the cell culture comprises at least about $1\times10^1$ APC hydrogel particles per mL of cell culture, e.g., at least about $1\times10^1$, at least about $1\times10^2$, at least about $1\times10^3$, at least about $1\times10^4$, at least about $1\times10^5$, at least about $1\times10^6$, at least about $1\times10^7$, at least about $1\times10^8$, at least about $1\times10^9$, at least about $1\times10^{10}$, at least about $1\times10^{11}$, at least about $1\times10^{12}$, at least about $1\times10^{13}$, at least about $1\times10^{14}$, at least about $1\times10^{15}$, at least about $1\times10^{16}$, at least about $1\times10^{17}$, at least about $1\times10^{18}$, at least about $1\times10^{19}$, at least about $1\times10^{20}$, or more. In some embodiments, the cell culture comprises from about $1\times10^5$ to about $1\times10^8$ APC hydrogel particles per mL of cell culture (e.g., $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, including all values and subranges therein). In some embodiments, the cell culture comprises about $1\times10^5$, about $1\times10^6$, about $1\times10^7$, or about $1\times10^8$ APC hydrogel particles per mL of cell culture. In some embodiments, the cell culture comprises a similar concentration of APC hydrogel particles as APC cells used in traditional cell culturing methods.

In some embodiments, the APC hydrogels of the present disclosure and T cells are cultured for at least about 30 minutes, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, 2, days, 36 hours, 3 days, 4 days, 5 days, 6 days, 7 days, 8 days, 9 days, 10 days, 11 days, 13 days, 14 days, or more, including all values and ranges therein.

Adoptive Cell Therapy

Provided are APC hydrogel particles, and cells produced therefrom, for adoptive cell therapy, e.g., adoptive immunotherapy. The cells include immune cells such as those described above, including T cells and NK cells, and generally express genetically engineered antigen receptors such as engineered TCRs and/or chimeric antigen receptors (CARs).

The hydrogels are engineered by introducing one or more antigens stimulate T cell expansion and/or activation. The antigens may interact with antigen receptors, including engineered T cell receptors (TCRs) and functional non-TCR antigen receptors, such as chimeric antigen receptors (CARs), including activating, stimulatory, and costimulatory CARs, and combinations thereof. In some embodiments, the cells cultured with the APC hydrogels disclosed herein express an engineered receptor targeting (e.g., specifically binding to or recognizing) an antigen, such as a disease-specific target antigen corresponding to the disease or condition to be treated.

In some embodiments, the adoptive cell therapy is tumor-infiltrating lymphocyte therapy. In tumor infiltrating lymphocyte therapy, naturally occurring T cells that have already infiltrated patients' tumors are harvested and cultured with the APC hydrogel particles described herein to activate and expand them. Activated T cells are then re-infused into patients, where they can then seek out and destroy tumors.

In some embodiments, the adoptive cell therapy is engineered T cell receptor (TCR) therapy. In TCR therapy, T cells from patients are harvested. The T cells are equipped (engineered) with an appropriate T cell receptor (e.g., as described herein) that enables them to target specific cancer antigens. The engineered T cells are then cultured with the APC hydrogel particles described herein to activate and expand them. Activated T cells are then re-infused into patients, where they can then seek out and destroy tumors.

In some embodiments, the adoptive cell therapy is chimeric antigen receptor (CAR) T cell therapy. In CAR T cell therapy, T cells from patients are harvested. T cells are collected via apheresis, a procedure during which blood is withdrawn from the body and one or more blood components (such as plasma, platelets or white blood cells) are removed. The remaining blood is then returned to the body. T cells are then reengineered in a laboratory. To this end, the T cells are sent to a laboratory or a drug manufacturing facility where they are genetically engineered, by introducing nucleic acids, RNA, and/or DNA into them, to produce chimeric antigen receptors (CARs) on the surface of the cells. After this reengineering, the T cells are known as "chimeric antigen receptor (CAR) T cells." CARs are proteins that allow the T cells to recognize an antigen on targeted tumor cells. The reengineered CAR T cells are then cultured with the APC hydrogel particles described herein to activate and expand them. The number of the patient's genetically modified T cells is "expanded" by growing cells in the laboratory. When there are enough of them, these CAR T cells are frozen and sent to the hospital or center where the patient is being treated. At the hospital or treatment center, the CAR T cells are thawed and then infused into the patient, where they can then seek out and destroy tumors. CARs can bind to cancer cells even if their antigens are not presented on the surface via major histocompatibility complex, which can render more cancer cells vulnerable to their attacks. Many patients are given a brief course of one or more chemotherapy agents, called "lymphodepletion," before they receive the infusion of CAR T cells. CAR T cells that have been returned to the patient's bloodstream multiply in number. These are the "attacker" cells that will recognize, and attack, cells that have the targeted antigen on their surface. In some embodiments, the adoptive cell therapy is natural killer (NK) cell therapy.

i. Cells, Cell Preparation, and Culture

In some embodiments, the cells are eukaryotic cells, such as mammalian cells, e.g., human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some embodiments, the cells are human cells. The cells typically are primary cells, such as those isolated directly from a subject and/or isolated from a subject and frozen. In some embodiments, the cells include one or more subsets of T cells or other cell types, such as whole T cell populations, CD4+ cells, CDS+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some embodiments, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CDS+ T cells are naive T (TN) cells, effector T cells (T EFF), memory T cells and sub-types thereof, such as stem cell memory T (T scM), central memory T (TcM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as THI cells, TH2 cells, TH3 cells, THI 7 cells, TH9 cells, TH22 cells, follicular helper T cells, alpha/beta T cells, and delta/gamma T cells.

In some embodiments, one or more of the T cell populations is enriched for or depleted of cells that are positive for (marker+) or express high levels (marker$^{high}$) of one or more particular markers, such as surface markers, or that are negative for (marker−) or express relatively low levels (marker$^{low}$) of one or more markers. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CDS+ cells or the T cells, e.g., CD3+ cells) are enriched for (i.e., positively selected for) cells that are positive or expressing high surface levels of CD45RO, CCR7, CD2S, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, and/or IL 7-Ra (CD127). In some examples, CDS+ T cells are enriched for cells positive for CD45RO (or negative for CD45RA) and for CD62L.

In some embodiments, a CD4+ T cell population and a CDS+ T cell sub-population, e.g., a sub-population enriched for central memory (T cM) cells. In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

ii. Cell Preparation

The cells typically are isolated from a sample, such as a biological sample, e.g., one obtained from or derived from a subject. In some embodiments, the subject from which the cell is isolated as one having a particular disease or condition or in need of a cell therapy or to which cell therapy will be administered. The subject in some embodiments is a mammal, such as a human, such as a subject in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g., transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some embodiments, the sample from which the cells are derived or isolated is blood or a blood-derived sample or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

iii. Incubation and Culture

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a genetically engineered antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded), and incubating the culture (e.g., for a time sufficient to expand the numbers of T cells). In some embodiments, the non-dividing feeder cells can comprise gamma irradiated PBMC feeder cells. In some embodiments, the PBMC are irradiated with ganma rays in the range of about 3000 to 3600 rads to prevent cell division. In some embodiments, the feeder cells are added to culture medium prior to the addition complex (MHC) molecule. Exemplary antigen receptors, including CARs and recombinant TCRs, as well as methods for engineering and introducing the receptors into cells.

In some embodiments, the T cells are expanded by cell culture with APC hydrogels, as described above. For instance, in some embodiments, the cell culture comprises at least about $1\times10^1$ APC hydrogel particles per mL of cell culture, e.g., at least about $1\times10^1$, at least about $1\times10^2$, at least about $1\times10^3$, at least about $1\times10^4$, at least about $1\times10^5$, at least about $1\times10^6$, at least about $1\times10^7$, at least about $1\times10^8$, at least about $1\times10^9$, at least about $1\times10^{10}$, at least about $1\times10^{11}$, at least about $1\times10^{12}$, at least about $1\times10^{13}$, at least about $1\times10^{14}$, at least about $1\times10^{15}$, at least about $1\times10^{16}$, at least about $1\times10^{17}$, at least about $1\times10^{18}$, at least about $1\times10^{19}$, at least about $1\times10^{20}$, or more. In some embodiments, the cell culture comprises from about $1\times10^5$ to about $1\times10^8$ APC hydrogel particles per mL of cell culture (e.g., $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, including all values and subranges therein). In some embodiments, the cell culture comprises about $1\times10^5$, about $1\times10^6$, about $1\times10^7$, or about $1\times10^8$ APC hydrogel particles per mL of cell culture.

In some embodiments, the APC hydrogels of the present disclosure and T cells are cultured for at least about 30 minutes, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, 2 days, 3, days, 4 days, 5 days, 6 days, 7 days, 8 days, 9 days, 10 days, 11 days, 13 days, 14 days, or more, including all values and ranges therein.

In some embodiments, the APC hydrogel particles of the present disclosure are applied to the cell culture at a dilution of about 1:1 to about 1:1000. In some embodiments, the APC hydrogel particles are applied to the cell culture at a dilution of about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, about 1:100, about 1:200, about 1:300, about 1:400, about 1:500, about 1:600, about 1:700, about 1:800, about 1:900, or about 1:1000.

In some embodiments, culturing the T cell with an APC hydrogel particle of the present disclosure increases T cell proliferation by about 1% to about 1000s % compared to culturing of the T cell without the APC hydrogel particle. In some embodiments, T cell proliferation is increased by about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, or about 1000% compared to culturing of the T cell without the APC hydrogel particle.

In some embodiments, culturing the T cell with an APC hydrogel particle of the present disclosure increases T cell activation by about 1% to about 1000% compared to culturing of the T cell without the APC hydrogel particle. In some embodiments, T cell activation is increased by about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, or about 1000% compared to culturing of the T cell without the APC hydrogel particle.

In some embodiments, culturing the T cell with an APC hydrogel particle of the present disclosure increases T cell expansion by about 1% to about 1000% compared to culturing of the T cell without the APC hydrogel particle. In some embodiments, T cell expansion is increased by about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, or about 1000% compared to culturing of the T cell without the APC hydrogel particle.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBY-transformed lymphoblastoid cells (LCL) as feeder cells. LCL can be irradiated with gamma rays in the range of about 6000 to 10,000 rads. The LCL feeder cells in some embodiments is provided in any suitable amount, such as a ratio of LCL feeder cells to initial T lymphocytes of at least about 10:1.

In embodiments, antigen-specific T cells, such as antigen specific CD4+ and/or CDS+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

In some embodiments, the methods include assessing expression of one or more markers on the surface of the engineered cells or cells being engineered. In one embodiment, the methods include assessing surface expression of one or more target antigen (e.g., antigen recognized by the genetically engineered antigen receptor) sought to be targeted by the adoptive cell therapy, for example, by affinity-based detection methods such as by flow cytometry. In some embodiments, where the method reveals surface expression of the antigen or other marker, the gene encoding the antigen or other marker is disrupted or expression otherwise repressed for example, using the methods described herein.

Examples of T Cell Activation

Many laboratories use CD3/CD28-activator magnetic beads for short- and long-term expansion of human primary T cells for research or clinical purposes. Without activation, T cells do not proliferate efficiently and, furthermore, their metabolically and epigenetically inactive profile makes them harder to manipulate. Different activation techniques can favor different T cell subtypes and therefore, the choice of the activation technique can be made based on the specific use case or experimental setup.

Activation with anti-CD3 and anti-CD28 coated beads is beneficial in cases where the polyclonal nature of the T cell population needs to be preserved, for example T cell expansion for adoptive cell therapy for cancer or infectious disease.

In an example, a hydrogel particle coated with anti-CD3 and anti-CD28 to stimulate activation of either naïve T cells or regulatory T cells was developed.

Naïve T cells are isolated using immunomagnetic methods and placed in culture media comprising rH IL2 in addition to hydrogel particles coated with anti-CD3 and anti-CD28 at various concentrations. The naïve T cells are cultured for 10-14 days (the "culture period") and activation assessed for expression of CD25 and CD69 on $CD4^+$ and $CD8^+$ subsets by flow cytometric methods. Fold expansion is calculated over the culture period. A greater than 10-fold expansion from the starting cell population, without a loss of CD4, CD8, CD69 or CD25 expression, as determined by phenotypic analysis, is observed.

Regulatory T cells (CD4+CD25hi) are isolated using immunomagnetic methods and placed in culture media comprising rH IL2 in addition to the hydrogels functionalized with anti-CD3 and anti-CD28 at various concentrations. The regulatory T cells are cultured for 10-14 days??? And activation assessed for expression of CD25 and CD69 on CD4+ and CD8+ subsets by flow cytometric methods. CD62L, HLA-DR, CCR6 and FOXP3 are assessed by flow cytometric analysis and fold expansion is calculated over the culture period. A greater than 10-fold expansion from the starting cell population, without a loss of CD25, CD69, HLA-DR, CCR6, and FOXP3 expression, is observed.

Adoptive cell therapy with autologous tumor infiltrating lymphocytes is a therapy for metastatic melanoma, and response rates to adoptive cell therapy have been reported to be up to 50%. However, the generation of the tumor infiltrating lymphocytes transfer product is challenging, requiring pooled allogeneic normal donor peripheral blood mononuclear cells (PBMC) used in vitro as "feeders" to support a rapid expansion protocol. Here, as an alternative to using PBMC feeders, a platform to propagate tumor infiltrating lymphocytes using hydrogels functionalized with costimulatory molecules such as CD86, CD137, and membrane-bound IL-15 to function as an artificial antigen-presenting cell.

The artificial antigen-presenting cell propagated tumor infiltrating lymphocytes can be measured against tumor infiltrating lymphocytes propagated with PBMC feeders, while increasing the frequency of CD8$^+$ T-cell expansion with a comparable effector-memory phenotype. Expansion of tumor infiltrating lymphocytes with the artificial antigen-presenting cell is expected to be equivalent or greater than the PBMC feeders cell system, without a loss of CD8$^+$ expression.

Kits

In some aspects, the present disclosure provides kits comprising one or more feeder hydrogel particles as disclosed herein. In some embodiments, the kit comprises feeder hydrogel particles that do not comprise one or more molecules that support cell growth and/or stimulate target cell proliferation or activation and instructions/reagents for attaching such molecules as desired.

NUMBERED EMBODIMENTS OF THE INVENTION

Notwithstanding the appended claims, the disclosure sets forth the following numbered embodiments:

(1) A hydrogel particle comprising one or more molecules that support at least one of supporting cell growth, increasing cell proliferation, or increasing activation of a target cell.

(2) The hydrogel particle of (1), wherein the one or more molecules include an interleukin, a member of the tumor necrosis factor superfamily, or both.

(3) The hydrogel particle of either (1) or (2), wherein the target cell is a stem cell or a lymphocyte.

(4) The hydrogel particle of any one of (1) to (3), wherein the lymphocyte is T cell or a natural killer cell.

(5) The hydrogel particle of any one of (1) to (4), wherein the one or more molecules include IL-2, IL-15, IL-21, CD137, CD137L, or a combination thereof.

(6) The hydrogel particle of any one of (1) to (5), further comprising a matrix including a monomer.

(7) The hydrogel particle of any one of (1) to (6), wherein the monomer is hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methacrylate, methacrylic acid, sodium methacrylate, glycerol methacrylate, hydroxypropyl methacrylate, hydroxybutyl methacrylate, phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide N-(4-methylphenyl) methyl acrylamide, N-1-naphthyl acrylamide, N-4-nitrophenyl acrylamide, N-(2-phenylethyl)acrylamide, N-triphenylmethyl acrylamide, N-(4-hydroxyphenyl)acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-(2-phenylethyl)methacrylamide, N-triphenylmethyl methacrylamide, N-(4-hydroxyphenyl)methacrylamide, N,N-methylphenyl methacrylamide, N,N'-phenyl phenylethyl methacrylamide, N-vinylcarbazole, 4-vinylpyridine, 2-vinylpyridine, or a combination thereof.

(8) The hydrogel particle of any one of (1) to (7), wherein the monomer is biodegradable.

(9) The hydrogel particle of any one of (1) to (8), wherein the biodegradable monomer is a monosaccharide, disaccharide, polysaccharide, peptide, protein, or protein domain.

(10) The hydrogel particle of any one of (1) to (9), wherein the biodegradable monomer is a protein, a protein domain comprising at least one non-natural amino acid, a proteoglycan, an extracellular matrix component, decorin, biglycan, testican, bikunin, fibromodulin, lumican, collage, elastin, collagen type I, collagen type II, collagen type III, a domain thereof, or a combination thereof.

(11) The hydrogel particle of any one of (1) to (10), wherein the biodegradable monomer is a structural polysaccharide.

(12) The hydrogel particle of any one of (1) to (11), wherein the biodegradable monomer is agar, agarose, alginic acid, alguronic acid, alpha glucan, amylopectin, amylose, arabinoxylan, beta-glucan, callose, capsullan, carrageenan polysaccharide, cellodextrin, cellulin, cellulose, chitin, chitosan, chrysolaminarin, curdlan, cyclodextrin, alpha-cyclodextrin, dextrin, dextran, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage glucan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, polylactide, polyglycolide, polycaprolactone, poly(lactic-co-glycolic) acid, and a copolymer, or a combination thereof.

(13) The hydrogel particle of any one of (1) to (12), wherein the monomer is functionalized.

(14) The hydrogel particle of any one of (1) to (13), wherein the monomer is functionalized with acrylate or acrylamide.

(15) The hydrogel particle of any one of (1) to (14), wherein the monomer is bifunctional.

(16) The hydrogel particle of any one of (1) to (15), wherein the hydrogel particle is functionalized on at least one surface.

(17) The hydrogel particle of any one of (1) to (16), further comprising a degradable matrix.

(18) The hydrogel particle of any one of (1) to (17), wherein the degradable matrix is configured to be broken down chemically, mechanically, or both.

(19) The hydrogel particle of any one of (1) to (18), wherein the one or more molecules are embedded or encapsulated within the degradable matrix.

(20) The hydrogel particle of any one of (1) to (19), wherein the degradable matrix includes at least one disulfide crosslink.

(21) The hydrogel particle of any one of (1) to (20), further comprising a plurality of layers, each layer being degradable and having a different rate of degradation.

(22) The hydrogel particle of any one of (1) to (21), wherein each of the plurality of layers includes the same type of the one or more molecules.

(23) The hydrogel particle of any one of (1) to (22), wherein each of the plurality of layers include a different type of the one or more molecules.

(24) The hydrogel particle of any one of (1) to (23), further comprising a matrix being composed of a magnetic material, having a magnetic material embedded or encapsulated within, or both, such that the matrix is capable of being attracted to or repelled by a magnetic field or a magnetic gradient introduced by a magnet.

(25) A method of at least one of supporting cell growth, increasing cell proliferation, or increasing activation of a target cell in culture comprising culturing the target cell with the hydrogel particle of any one of (1) to (24).

(26) A kit comprising a first hydrogel particle including one or more molecules that support at least one of supporting cell growth, increasing cell proliferation, or increasing activation of at least one of a plurality of target cells, and a second hydrogel particle including one or more molecules that support at least one of supporting cell growth, increasing cell proliferation, or increasing activation of at least one of the plurality of target cells.

(27) The kit of (26), further comprising a culture including the plurality of target cells.

(28) The kit of either (26) or (27), wherein the one or more molecules of the first hydrogel particle and the one or more molecules of the second hydrogel particle are different types of molecules.

(29) The kit of any one of (26) to (27), wherein the at least one of a plurality of target cells supported by the first hydrogel particle is a different type of cell than the at least one of a plurality of target cells supported by the second hydrogel particle.

(30) The kit of any one of (26) to (29), wherein the first and second hydrogel particles are degradable and have different rates of degradation.

The invention claimed is:

1. A magnetic capture hydrogel particle, comprising:
    a) a hydrogel matrix, said hydrogel matrix comprising a magnetic material embedded and/or encapsulated therein, such that the hydrogel particle is capable of being attracted to or repelled by a magnetic field; and
    b) a ligand capable of binding the hydrogel matrix to a capture target molecule,
    wherein the magnetic capture hydrogel particle is spherical and has a diameter of between about 2 μm and about 5 μm.

2. The magnetic capture hydrogel particle of claim 1, wherein the hydrogel matrix comprises a polymerized monomer and a bifunctional monomer.

3. The magnetic capture hydrogel particle of claim 2, wherein the monomer comprises acrylate or acrylamide.

4. The magnetic capture hydrogel particle of claim 2, wherein the monomer is selected from the group consisting of hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly (ethylene glycol) methacrylate, methoxy-poly (ethylene glycol) methacrylate, methacrylic acid, sodium methacrylate, glycerol methacrylate, hydroxypropyl methacrylate, hydroxybutyl methacrylate, phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide N-(4-methylphenyl) methyl acrylamide, N-1-naphthyl acrylamide, N-4-nitrophenyl acrylamide, N-(2-phenylethyl) acrylamide, N-triphenylmethyl acrylamide, N-(4-hydroxyphenyl) acrylamide, N,N-methylphenyl acrylamide, N,N-phenyl phenylethyl acrylamide, N-diphenylmethyl methacrylamide, N-(4-methyl phenyl) methyl methacrylamide, N-1-naphthyl methacrylamide, N-4-nitrophenyl methacrylamide, N-(2-phenylethyl) methacrylamide, N-triphenylmethyl methacrylamide, N-(4-hydroxyphenyl) methacrylamide, N,N-methylphenyl methacrylamide, N,N'-phenyl phenylethyl methacrylamide, N-vinylcarbazole, 4-vinylpyridine, 2-vinylpyridine, and a combination thereof.

5. The magnetic capture hydrogel particle of claim 2, wherein the monomer is selected from the group consisting of N,N'-methylenebisacrylamide, N,N'methylene bismethacrylamide, N,N'-ethylene bisacrylamide, N,N'-ethylene bismethacrylamide, N,N'propylenebisacrylamide, and N,N'-(1,2-dihydroxyethylene) bisacrylamide.

6. The magnetic capture hydrogel particle of claim 1, wherein the capture target molecule is on a cell selected from the group consisting of a B cell, a T cell, a natural killer cell, a lymphokine-activated killer cell, a monocyte, a macrophage, a neutrophil, a granulocyte, a mast cell, a platelet, a Langerhans cell, a stem cell, a dendritic cell, a peripheral blood mononuclear cell, a tumor infiltrating (TIL) cell, gene modified immune cells including hybridomas, drug modified immune cells, and combinations thereof.

7. The magnetic capture hydrogel particle of claim 1, wherein the capture target molecule is a biomarker.

8. The magnetic capture hydrogel particle of claim 1, wherein the capture target molecule is selected from the group consisting of CD2, CD3, CD4, CD8, CD19, CD20, CD25, CD27, CD28, CD30, CD40, CD40L, CD45RO, CD62L, CD69, CD62L, CD80, CD84, CD86, CD95, CD122, CD127, CD134, CD137, CD137L, CD150, CD154, CD226, CD229, CD244, CD270, CD278, CD319, CD352, CD355, CD357, membrane-bound IL-15, HLA-DR, CCR6, and FOXP3.

9. The magnetic capture hydrogel particle of claim 1, wherein the hydrogel matrix is degradable.

10. The magnetic capture hydrogel particle of claim 9, wherein the degradable matrix includes at least one disulfide crosslink.

11. The magnetic capture hydrogel particle of claim 1, wherein the ligand is an antibody or antigen-binding fragment thereof.

12. A method for separating a target molecule from an aqueous mixture, the method comprising:
 a) incubating an aqueous mixture comprising a target molecule and a magnetic capture hydrogel particle, thereby producing a target molecule-bound magnetic capture hydrogel particle, wherein the magnetic capture hydrogel particle comprises:
  i) a hydrogel matrix comprising a magnetic material embedded and/or encapsulated therein, such that the hydrogel particle is capable of being attracted to or repelled by a magnetic field; and
  ii) a ligand capable of binding the hydrogel matrix to the target molecule, wherein the magnetic capture hydrogel particle is spherical and has a diameter of between about 2 μm and about 5 μm;
 b) applying a magnetic field to the incubated aqueous mixture to isolate the target molecule-bound magnetic capture hydrogel particle from the aqueous mixture; and
 c) retrieving the isolated target molecule-bound magnetic capture hydrogel particle.

13. The method of claim 12, comprising step:
 d) separating, the target molecule from the magnetic capture hydrogel particle.

14. The method of claim 13, wherein the separating comprises dissolving the magnetic capture hydrogel particle.

15. The method of claim 13, wherein the dissolving the magnetic capture hydrogel particle comprises exposing the magnetic capture hydrogel particle to a disulfide reducing agent.

16. The method of claim 13, wherein the separating comprises cleaving the target molecule from the magnetic capture hydrogel particle.

17. A method for separating a target cell from an aqueous mixture, the method comprising:
 a) incubating an aqueous mixture comprising a target cell and a magnetic capture hydrogel particle, thereby producing a target cell-bound magnetic capture hydrogel particle, wherein the magnetic capture hydrogel particle comprises:
  i) a hydrogel matrix comprising a magnetic material embedded and/or encapsulated therein, such that the magnetic capture hydrogel particle is capable of being attracted to or repelled by a magnetic field; and
  ii) a ligand capable of binding the hydrogel matrix to the target cell, wherein the magnetic capture hydrogel particle is spherical and has a diameter of between about 2 μm and about 5 μm;
 b) applying a magnetic field to the incubated aqueous mixture to isolate the target cell-bound magnetic capture hydrogel particle from the aqueous mixture; and
 c) retrieving the isolated target cell-bound magnetic capture hydrogel particle.

* * * * *